US012735417B2

(12) United States Patent
Kordic et al.

(10) Patent No.: US 12,735,417 B2
(45) Date of Patent: Sep. 15, 2026

(54) SOLID STATE FORMS OF AMG-510 AND PROCESS FOR PREPARATION THEREOF

(71) Applicant: ASSIA CHEMICAL INDUSTRIES LTD., Tel Aviv (IL)

(72) Inventors: Lorena Kordic, Rab (HR); Sanja Matecic Musanic, Zagreb (HR)

(73) Assignee: ASSIA CHEMICAL INDUSTRIES LTD., Tel Aviv (IL)

( * ) Notice: Subject to any disclaimer, the term of this patent is extended or adjusted under 35 U.S.C. 154(b) by 671 days.

(21) Appl. No.: 17/925,845

(22) PCT Filed: May 20, 2021

(86) PCT No.: PCT/US2021/033388
§ 371 (c)(1),
(2) Date: Nov. 17, 2022

(87) PCT Pub. No.: WO2021/236920
PCT Pub. Date: Nov. 25, 2021

(65) Prior Publication Data

US 2023/0183235 A1 Jun. 15, 2023

Related U.S. Application Data

(60) Provisional application No. 63/087,382, filed on Oct. 5, 2020, provisional application No. 63/072,301, filed on Aug. 31, 2020, provisional application No. 63/059,372, filed on Jul. 31, 2020, provisional application No. 63/035,940, filed on Jun. 8, 2020, provisional application No. 63/027,494, filed on May 20, 2020.

(51) Int. Cl.
*C07D 471/04* (2006.01)

(52) U.S. Cl.
CPC ........ *C07D 471/04* (2013.01); *C07B 2200/13* (2013.01)

(58) Field of Classification Search
CPC .... A61P 35/00; C07B 2200/13; C07D 471/04
See application file for complete search history.

(56) References Cited

U.S. PATENT DOCUMENTS

| | | | | |
|---|---|---|---|---|
| 11,236,091 | B2 | 2/2022 | Chaves et al. | |
| 11,827,635 | B2 * | 11/2023 | Chaves | C07D 471/04 |
| 2018/0334454 | A1 * | 11/2018 | Lanman | C07D 403/04 |

FOREIGN PATENT DOCUMENTS

| | | | |
|---|---|---|---|
| JP | 2023544775 | A | 10/2023 |
| WO | 2018217651 | A1 | 11/2018 |
| WO | 2020102730 | A1 | 5/2020 |
| WO | 2020236947 | A1 | 11/2020 |
| WO | 2020236948 | A1 | 11/2020 |
| WO | 2022076623 | A1 | 4/2022 |

OTHER PUBLICATIONS

J. Med. Chem. (2019), vol. 63, p. 52-65 (Year: 2019).*

U.S. Pat. No. 11,827,635 B2 with appended priorirty document (U.S. Appl. No. 62/851,044) (Year: 2019).*

Brian A. Lanman et al, "Discovery of a Covalent Inhibitor of KRASG12C (AMG 510) for the Treatment of Solid Tumors", Journal of Medicinal Chemistry, vol. 63, pp. 52-65 (2020).

International Search Report and Written Opinion of the International Searching Authority issued in corresponding application PCT/US2021/033388 mailed Oct. 5, 2021 (16 pages).

Kazuhide Ashizawa, The Chemistry of Polymorphism and Crystallization of the Pharmaceutical Drugs, 2002, pp. 273, 278, 305-317 (English translation not available. Statement of Relevance can be found in the attached IDS Transmittal Letter.).

Office Action issued in corresponding Japanese Application No. 2023-571685 mailed Dec. 2, 2025, together with English language translation.

Pharmacia, 2016, vol. 52, No. 5, pp. 387-391 (English translation not available. Statement of Relevance can be found in the attached IDS Transmittal Letter.).

* cited by examiner

*Primary Examiner* — Fereydoun G Sajjadi
*Assistant Examiner* — Anna Grace Kuckla
(74) *Attorney, Agent, or Firm* — Carter, DeLuca & Farrell LLP

(57) ABSTRACT

The present disclosure encompasses solid state forms of AMG-510 (Sotorasib), in embodiments crystalline polymorphs of AMG-510, processes for preparation thereof, and pharmaceutical compositions thereof.

(I)

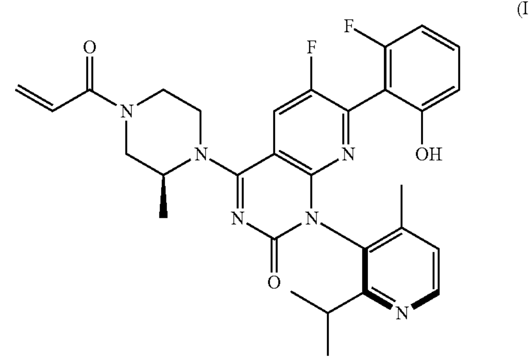

14 Claims, 19 Drawing Sheets

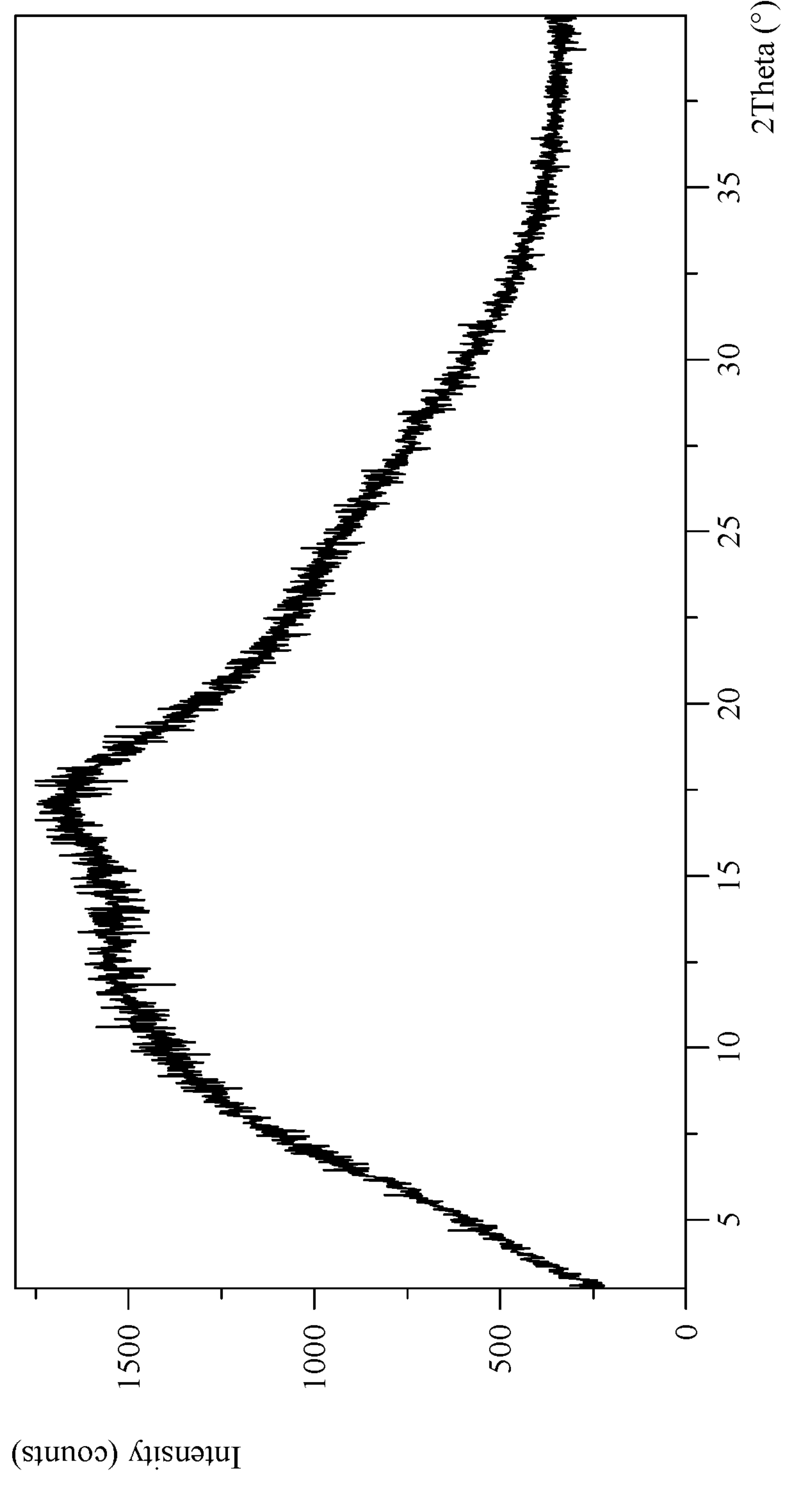
Figure 1. XRPD pattern of AMG-510, amorphous.

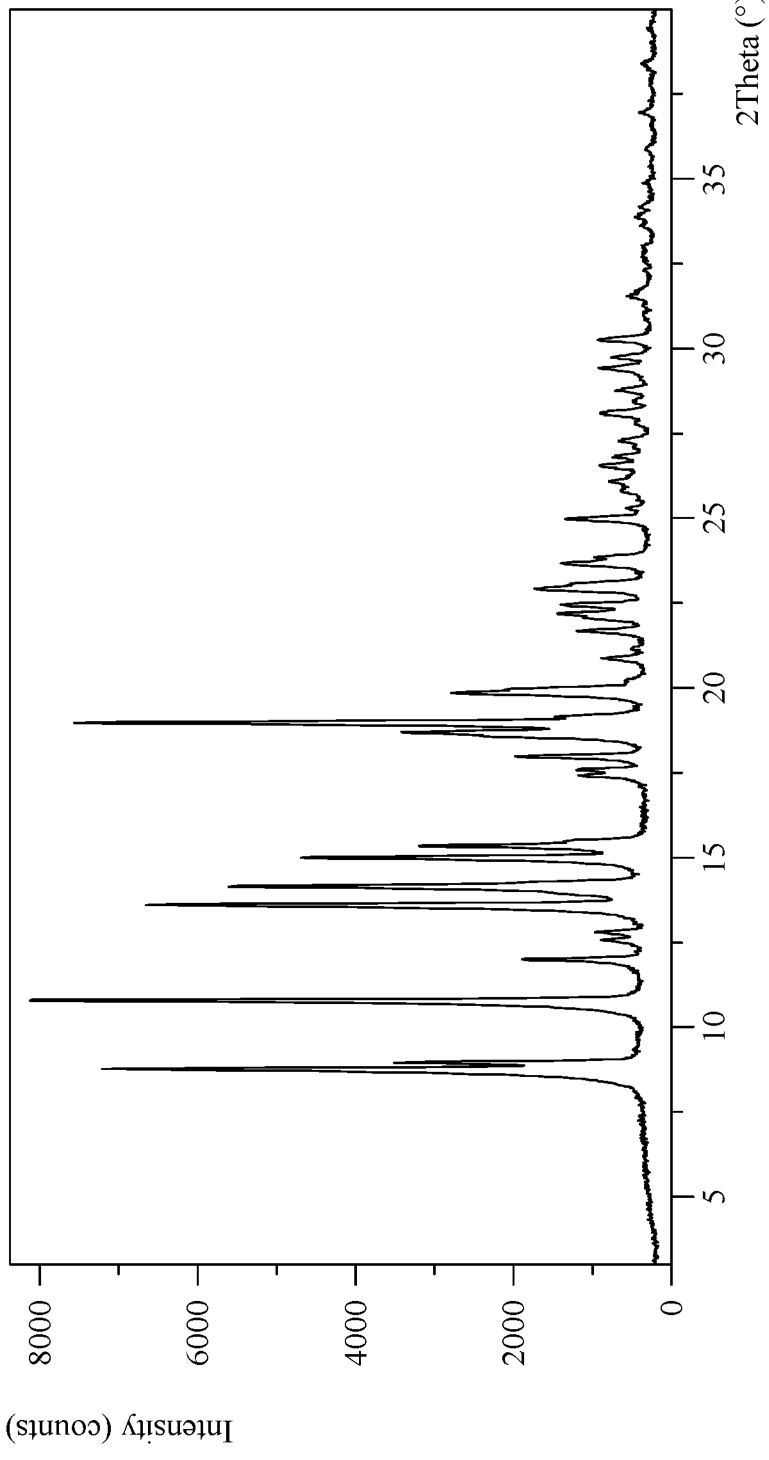
Figure 2. XRPD pattern of AMG-510, Form 1.

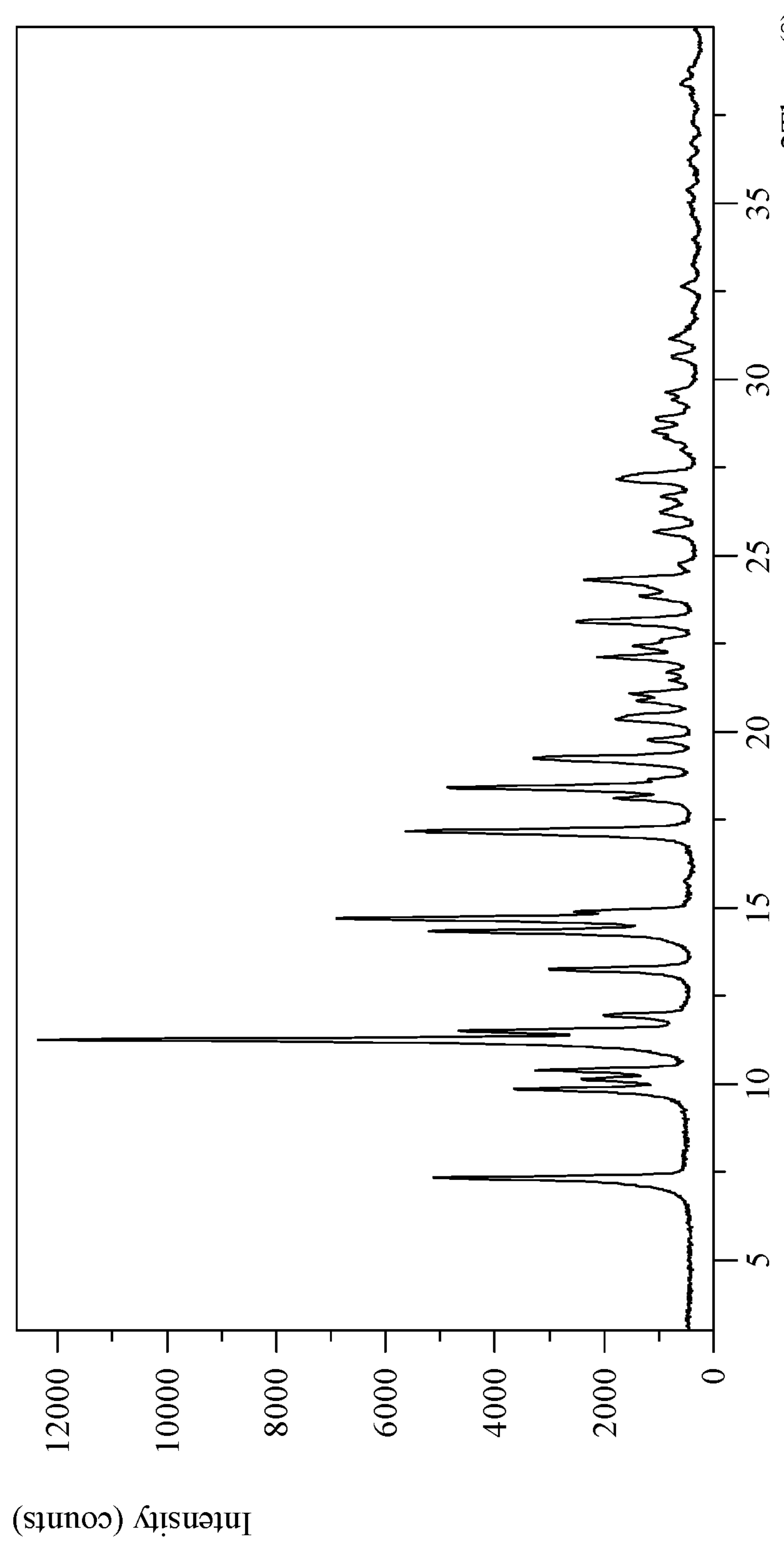
Figure 3. XRPD pattern of AMG-510, Form 2.

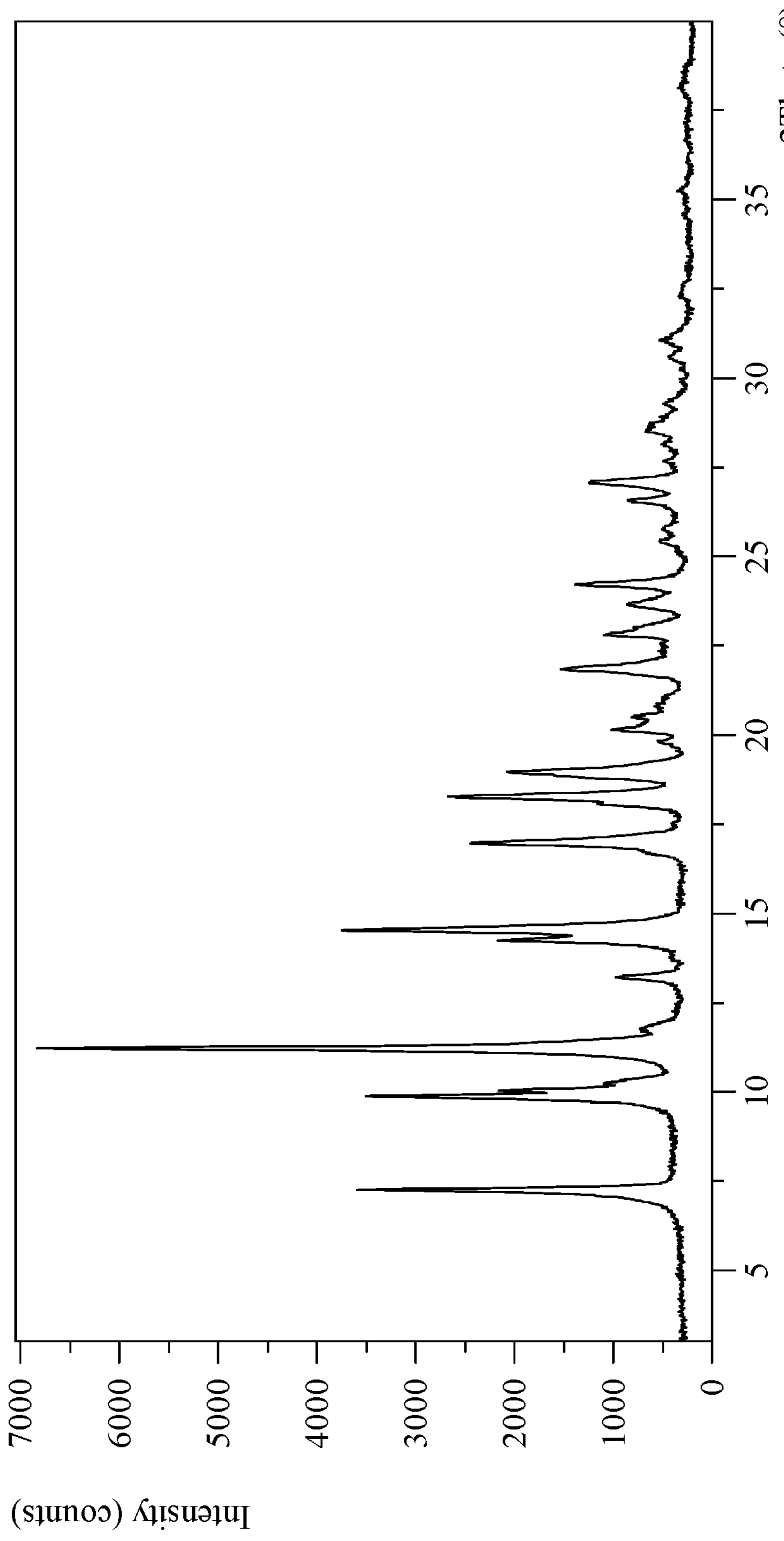
Figure 4. XRPD pattern of AMG-510, Form A.

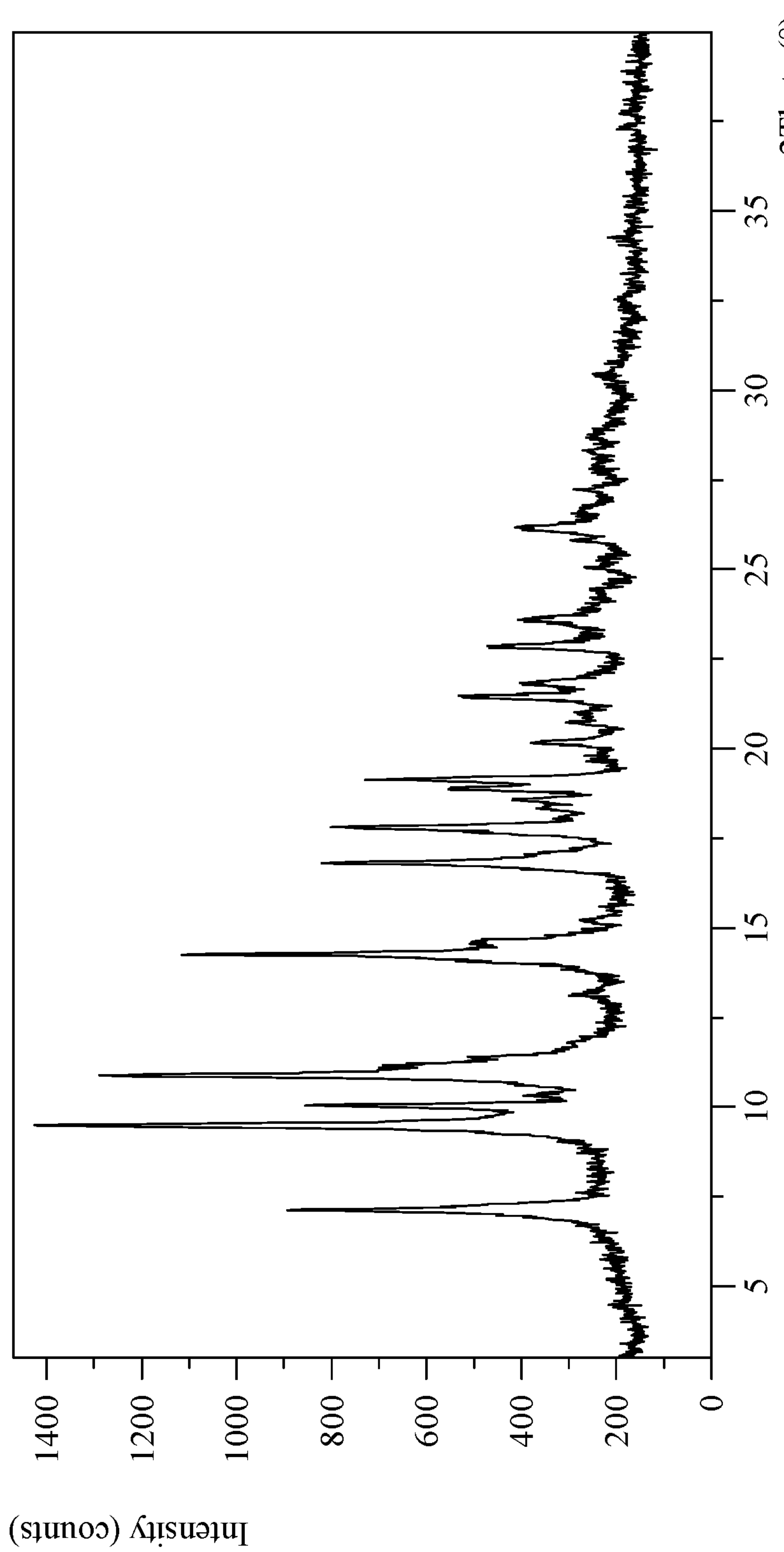
Figure 5. XRPD pattern of AMG-510, Form B.

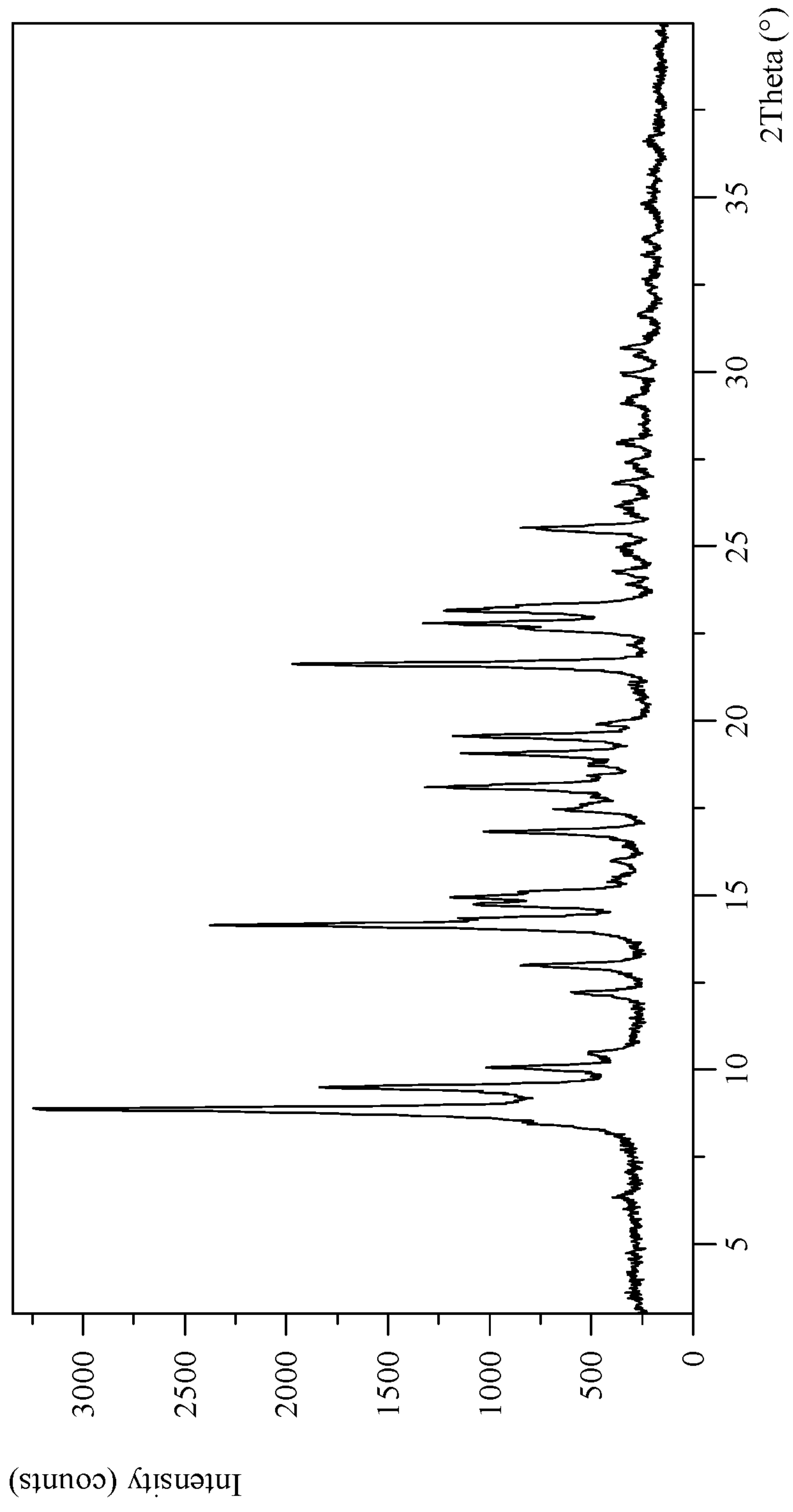
Figure 6. XRPD pattern of AMG-510, Form H1

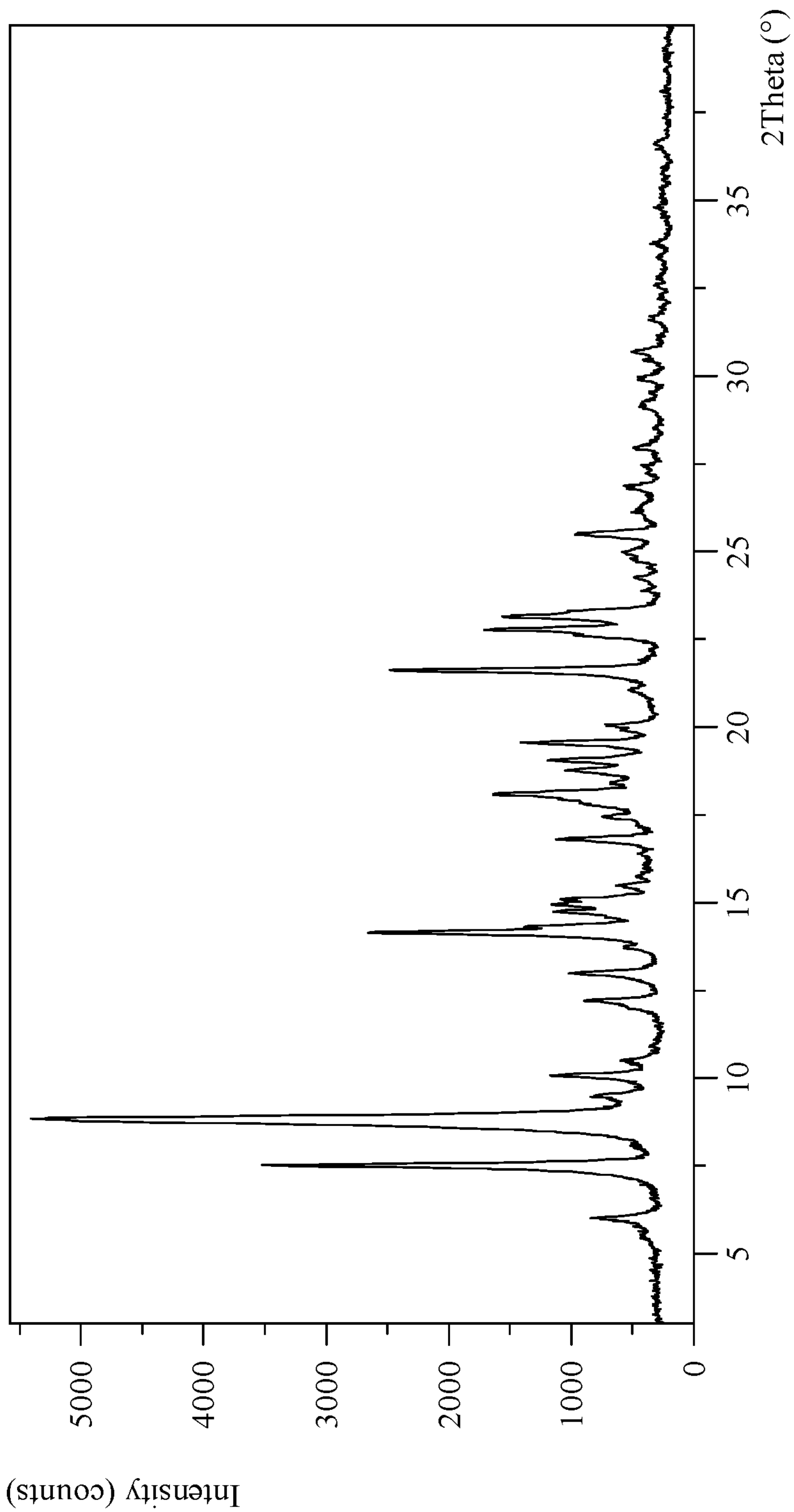
Figure 7. XRPD pattern of AMG-510, Form H2

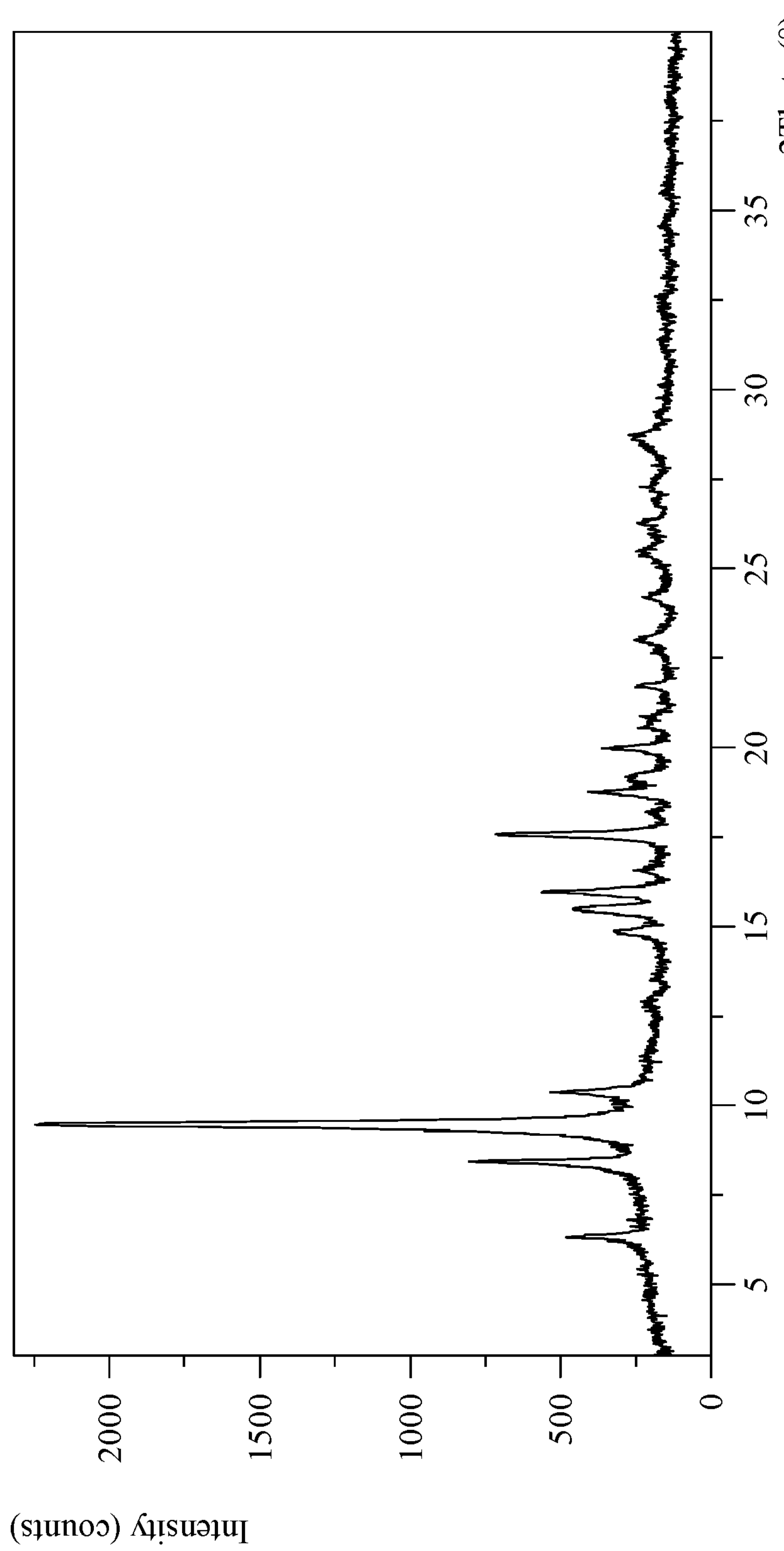
Figure 8. XRPD pattern of AMG-510, Form 3

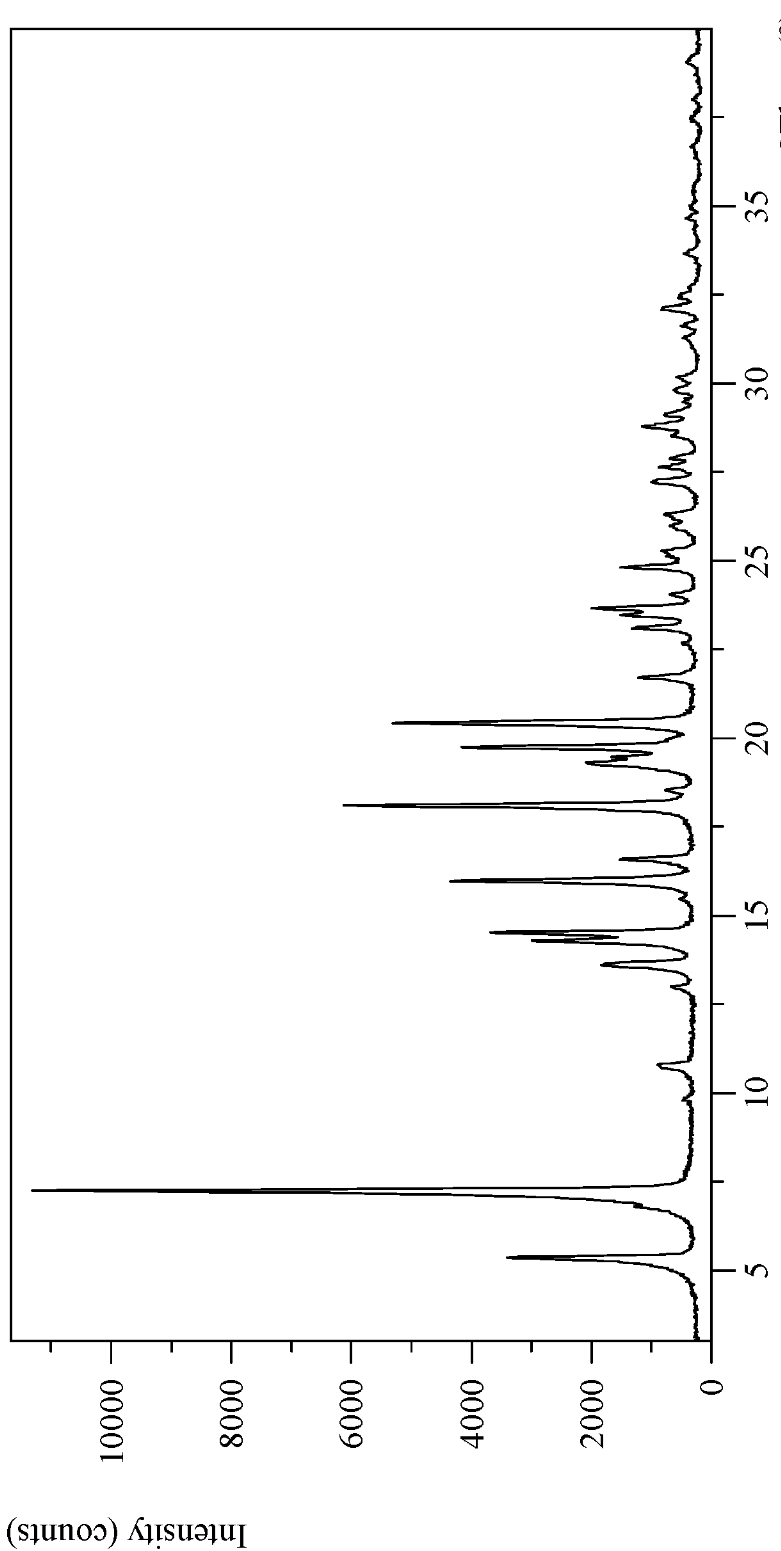
Figure 9. XRPD pattern of AMG-510, Form H3

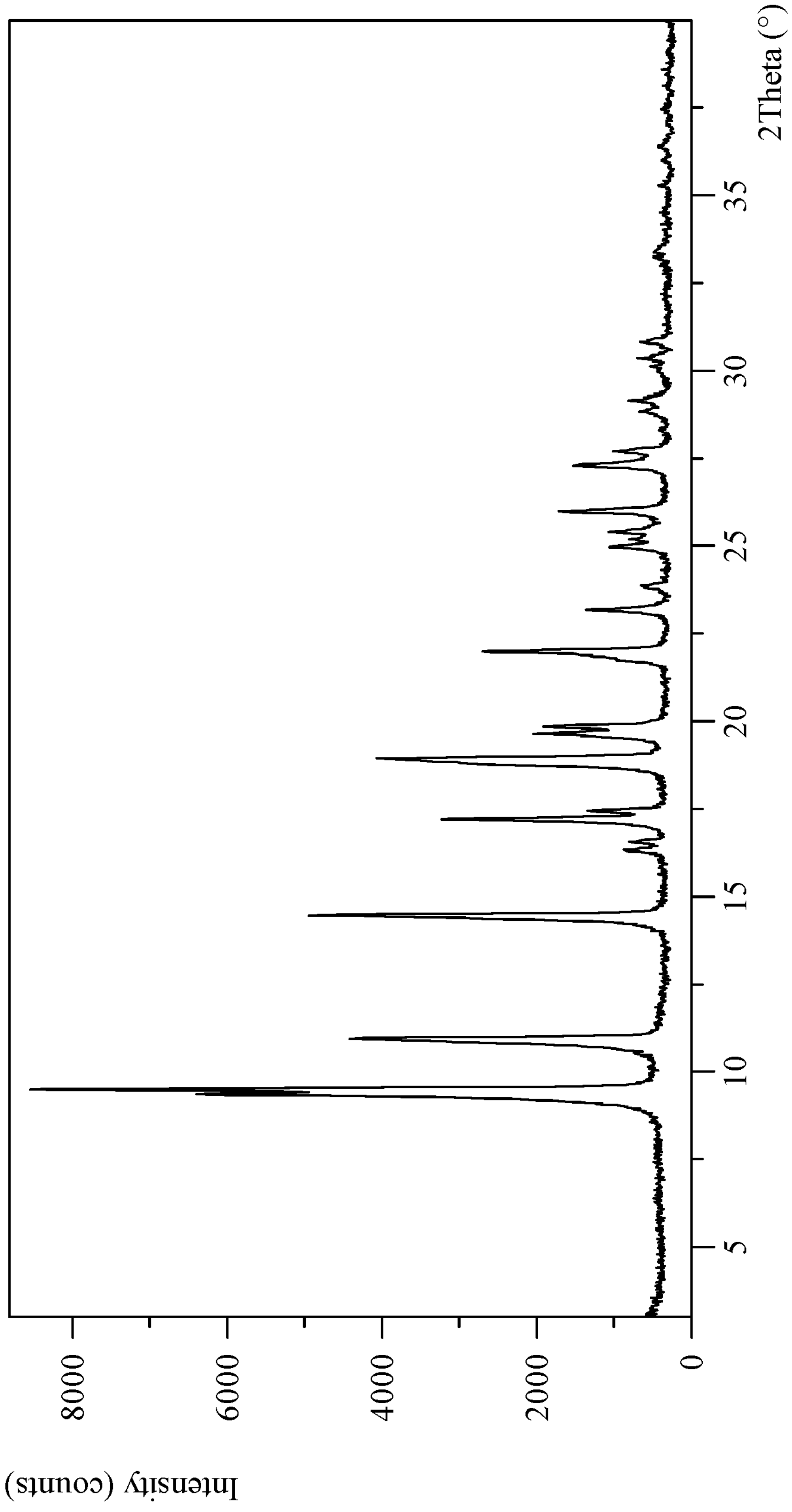
Figure 10. XRPD pattern of AMG-510:succinic acid, Form S1

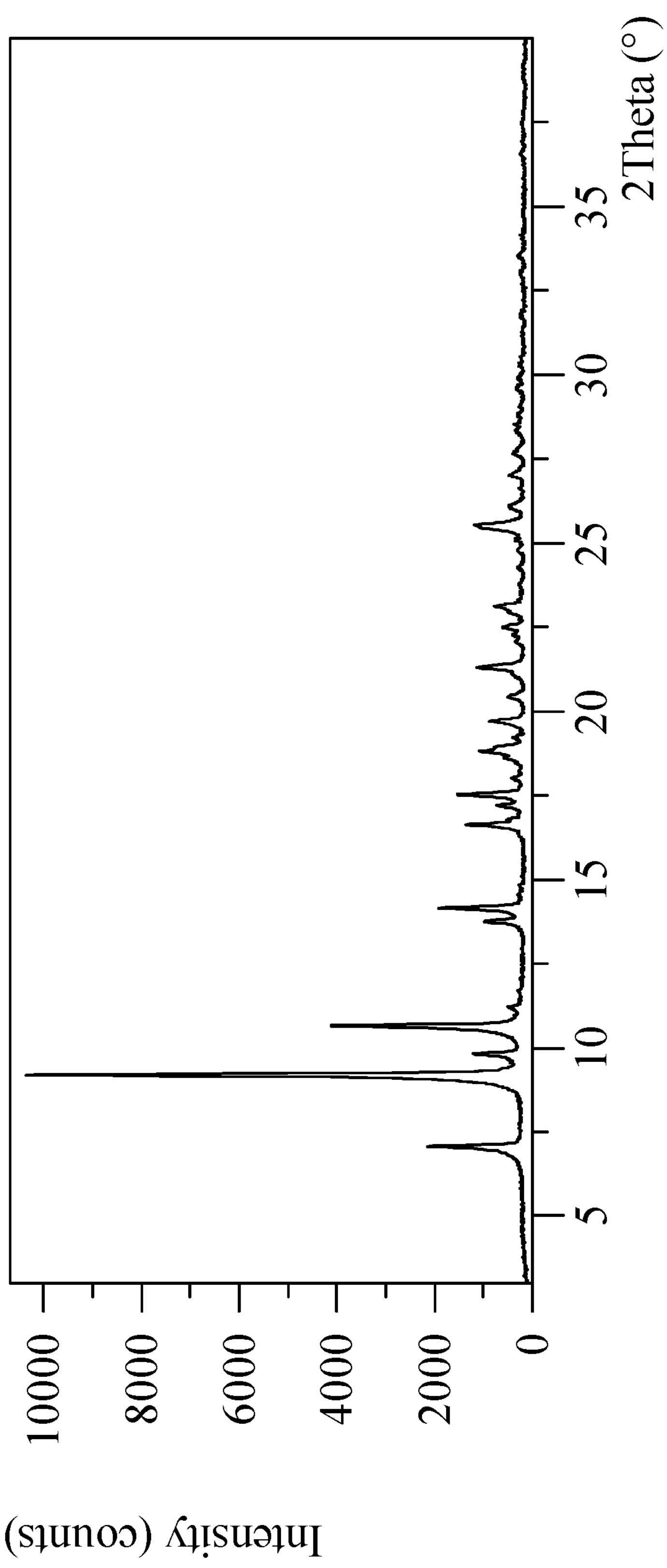
Figure 11. XRPD pattern of AMG-510, Form C1

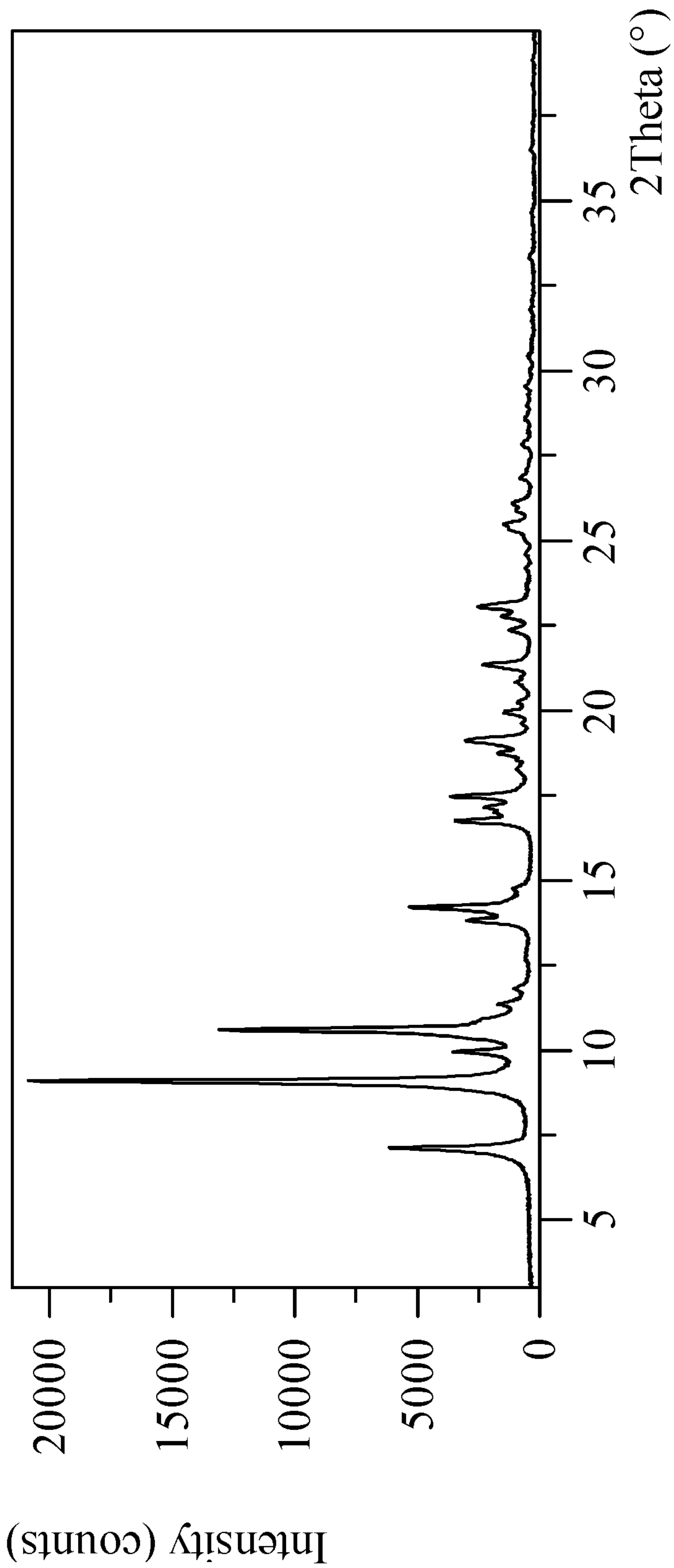
Figure 12. XRPD pattern of AMG-510, Form C2

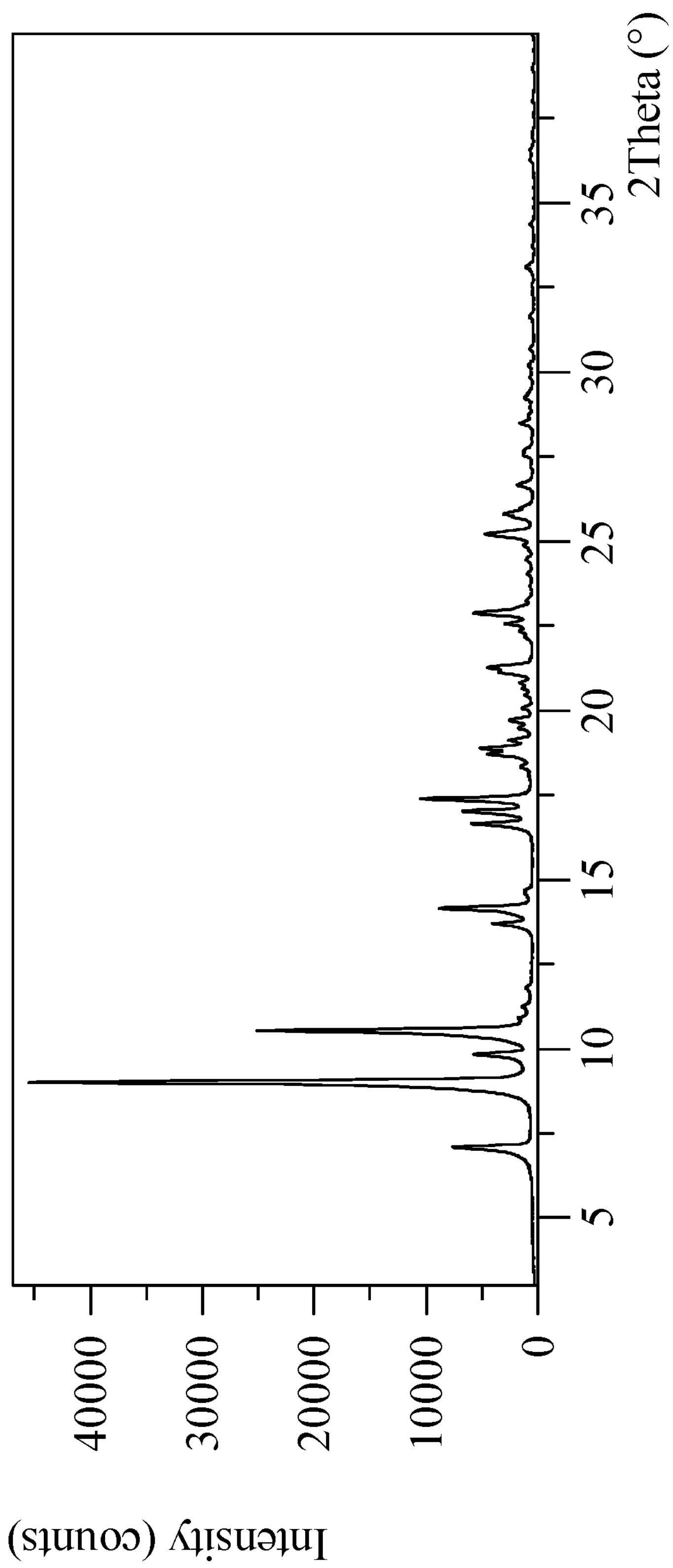
Figure 13. XRPD pattern of AMG-510, Form C3

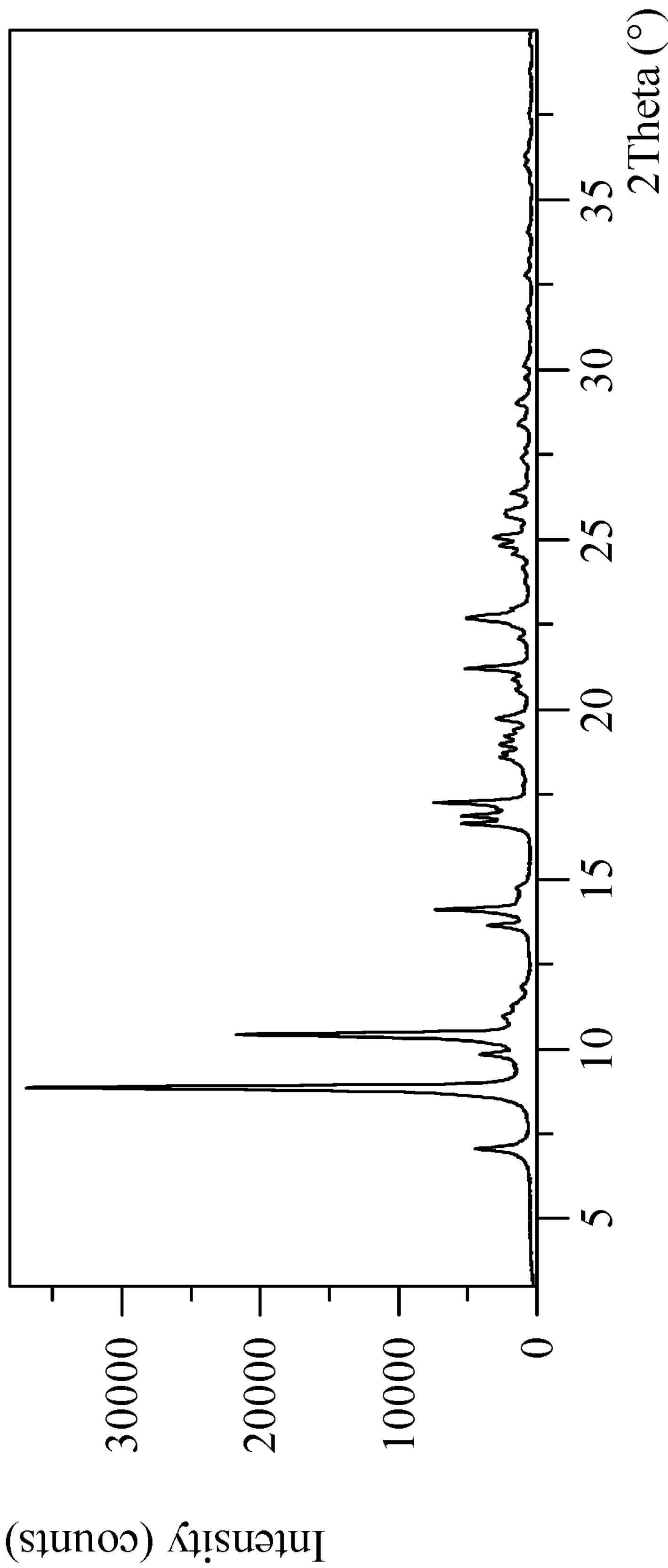
Figure 14. XRPD pattern of AMG-510, Form C4

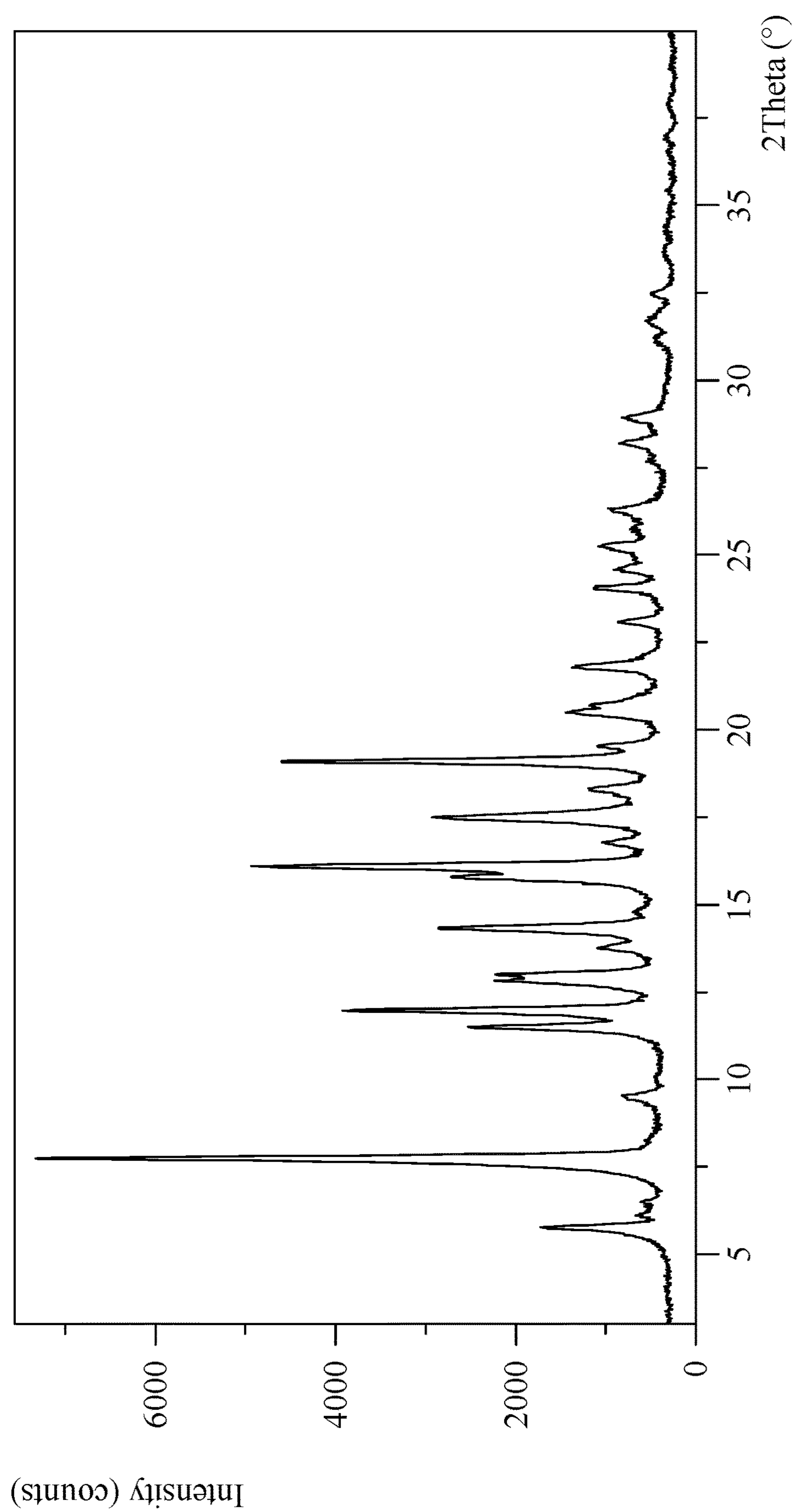
Figure 15. XRPD pattern of AMG-510, Form H4

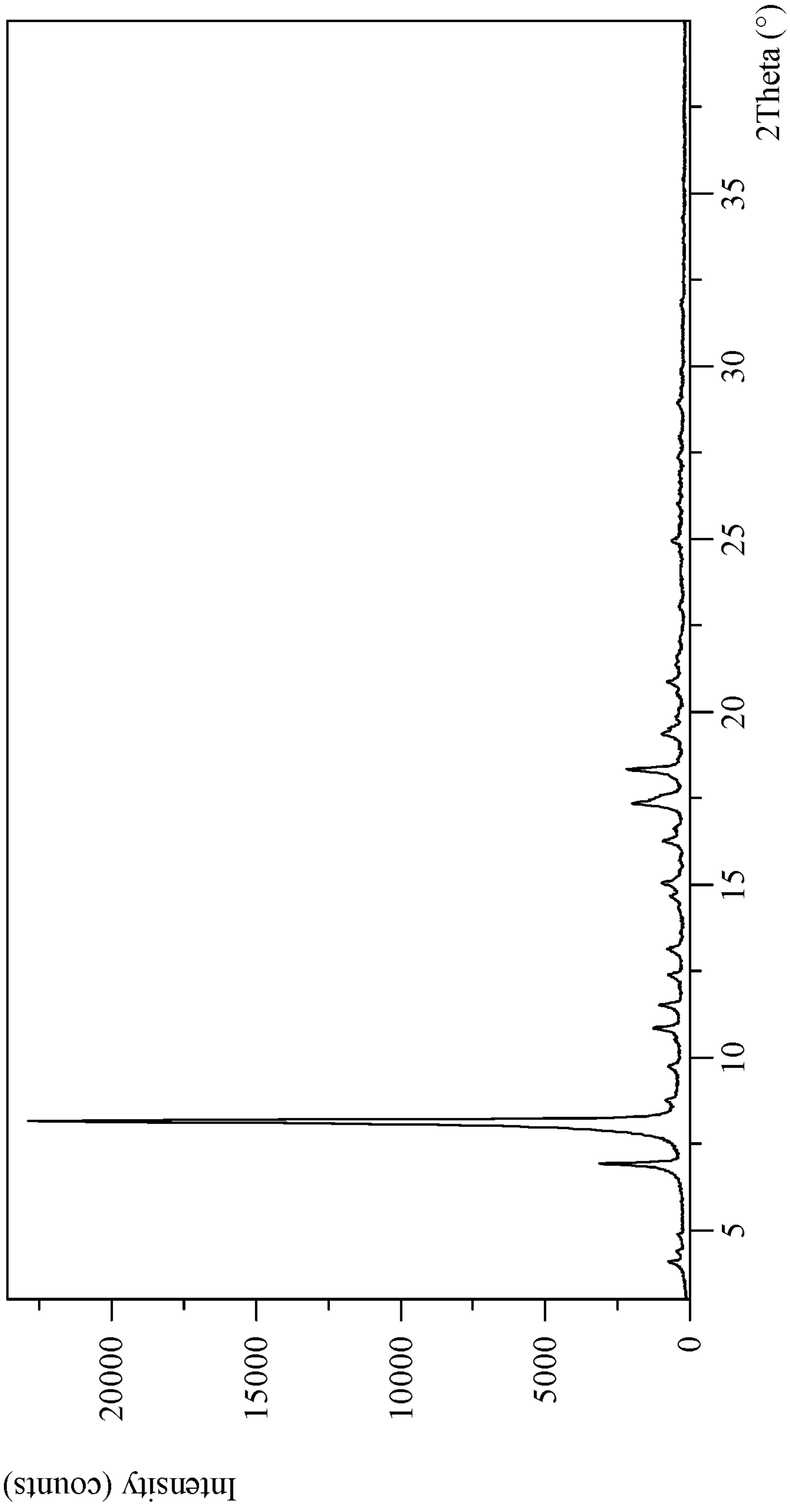
Figure 16. XRPD pattern of AMG-510, Form D

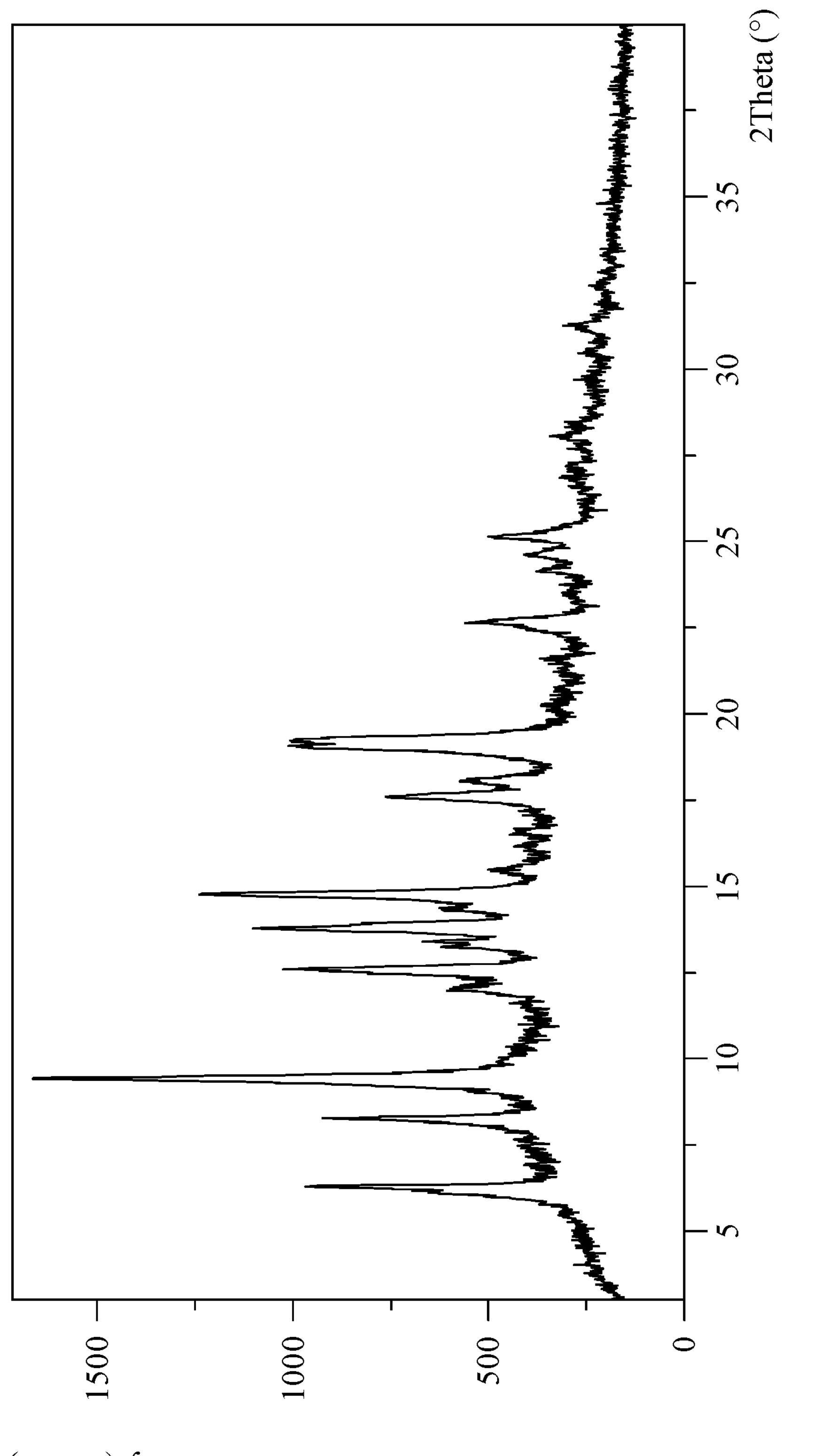
Figure 17. XRPD pattern of AMG-510, Form 4

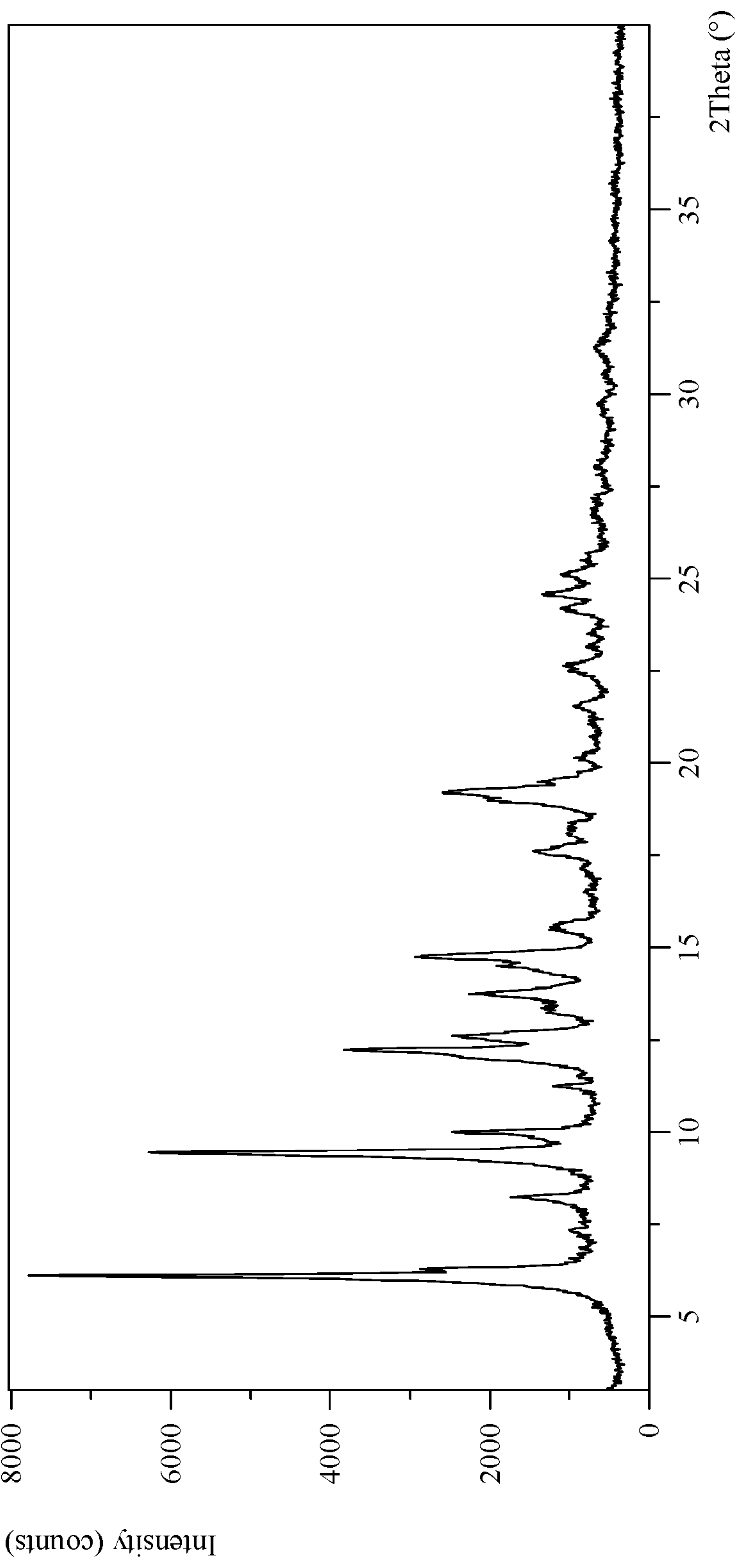
Figure 18. XRPD pattern of AMG-510, Form 4

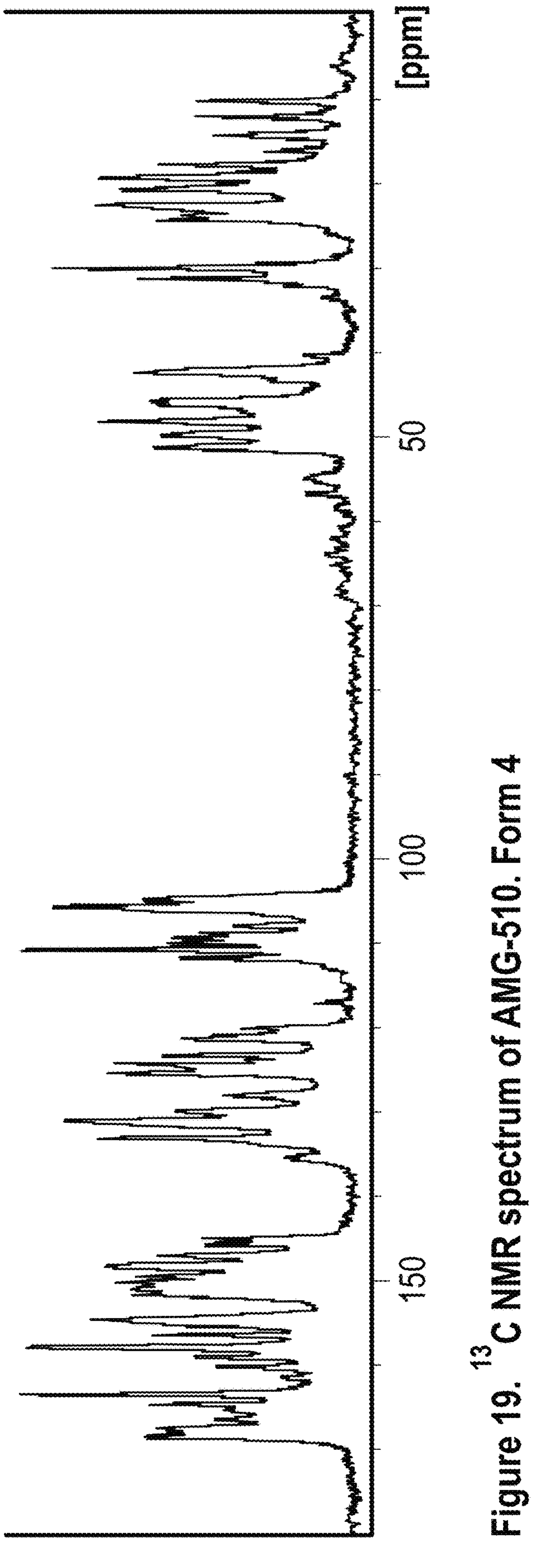
Figure 19. $^{13}C$ NMR spectrum of AMG-510. Form 4

SOLID STATE FORMS OF AMG-510 AND PROCESS FOR PREPARATION THEREOF

CROSS REFERENCE TO RELATED APPLICATIONS

This application is a National Stage of, and claims priority to and the benefit of, International Patent Application No. PCT/US2021/033388, filed May 20, 2021, which, in turn, claims the benefit of and priority to, U.S. Provisional Application No. 63/027,494, filed May 20, 2020; U.S. Provisional Application No. 63/035,940, filed Jun. 8, 2020; U.S. Provisional Application No. 63/059,372, filed Jul. 31, 2020; U.S. Provisional Application No. 63/072,301, filed Aug. 31, 2020; and U.S. Provisional Application No. 63/087,382, filed Oct. 5, 2020, the entire disclosures of each of which are incorporated by reference herein.

FIELD OF THE DISCLOSURE

The present disclosure encompasses solid state forms of AMG-510, in embodiments crystalline polymorphs of AMG-510, processes for preparation thereof, and pharmaceutical compositions thereof.

BACKGROUND OF THE DISCLOSURE

AMG-510, 6-fluoro-7-(2-fluoro-6-hydroxyphenyl)-1-[4-methyl-2-(propan-2-yl)pyridin-3-yl]-4-[(2S)-2-methyl-4-(prop-2-enoyl)piperazin-1-yl]-1H,2H-pyrido[2,3-d]pyrimidin-2-one (Sotorasib), has the following chemical structure:

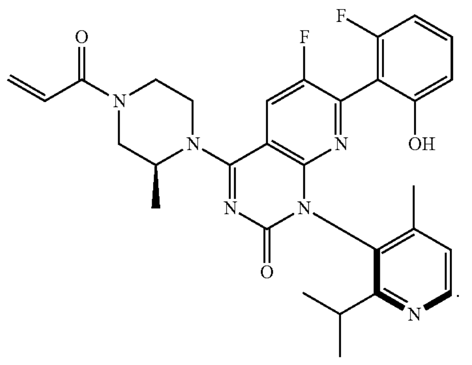

AMG-510, is reported to be a $KRAS^{G12C}$ small molecule inhibitor. It is being investigated in a Phase 2 study for non-small cell lung and colorectal cancers.

The compound is described in U.S. Pat. No. 10,519,146.

Polymorphism, the occurrence of different crystalline forms, is a property of some molecules and molecular complexes. A single molecule may give rise to a variety of polymorphs having distinct crystal structures and physical properties like melting point, thermal behaviors (e.g., measured by thermogravimetric analysis ("TGA"), or differential scanning calorimetry ("DSC")), X-ray diffraction (XRD) pattern, infrared absorption fingerprint, and solid state ($^{13}C$) NMR spectrum. One or more of these techniques may be used to distinguish different polymorphic forms of a compound.

Different salts and solid state forms (including solvated forms) of an active pharmaceutical ingredient may possess different properties. Such variations in the properties of different salts and solid state forms and solvates may provide a basis for improving formulation, for example, by facilitating better processing or handling characteristics, changing the dissolution profile in a favorable direction, or improving stability (polymorph as well as chemical stability) and shelf-life. These variations in the properties of different salts and solid state forms may also offer improvements to the final dosage form, for instance, if they serve to improve bioavailability. Different salts and solid state forms and solvates of an active pharmaceutical ingredient may also give rise to a variety of polymorphs or crystalline forms, which may in turn provide additional opportunities to assess variations in the properties and characteristics of a solid active pharmaceutical ingredient.

Discovering new solid state forms and solvates of a pharmaceutical product may yield materials having desirable processing properties, such as ease of handling, ease of processing, storage stability, and ease of purification or as desirable intermediate crystal forms that facilitate conversion to other polymorphic forms. New solid state forms of a pharmaceutically useful compound can also provide an opportunity to improve the performance characteristics of a pharmaceutical product. It enlarges the repertoire of materials that a formulation scientist has available for formulation optimization, for example by providing a product with different properties, including a different crystal habit, higher crystallinity, or polymorphic stability, which may offer better processing or handling characteristics, improved dissolution profile, or improved shelf-life (chemical/physical stability). For at least these reasons, there is a need for additional solid state forms (including solvated forms) of AMG-510.

SUMMARY OF THE DISCLOSURE

The present disclosure provides solid state forms of AMG-510 and salts thereof, in embodiments crystalline polymorphs of AMG-510, cocrystals of AMG-510 processes for preparation thereof, and pharmaceutical compositions thereof. These solid state forms can be used to prepare other solid state forms of AMG-510, AMG-510 salts and their solid state forms.

The present disclosure also provides uses of the said solid state forms of AMG-510 in the preparation of other solid state forms of AMG-510 or salts thereof.

The present disclosure provides solid state forms of AMG-510 for use in medicine, including for the treatment of cancer, in particular non-small cell lung and/or colorectal cancers.

The present disclosure also encompasses the use of solid state forms of AMG-510 of the present disclosure for the preparation of pharmaceutical compositions and/or formulations.

In another aspect, the present disclosure provides pharmaceutical compositions comprising solid state forms of AMG-510 according to the present disclosure.

The present disclosure includes processes for preparing the above mentioned pharmaceutical compositions. The processes include combining any one or a combination of the solid state forms of AMG-510 with at least one pharmaceutically acceptable excipient.

The solid state forms of AMG-510 as defined herein and the pharmaceutical compositions or formulations of the solid state forms of AMG-510 may be used as medicaments, such as for the treatment of cancer, in particular non-small cell lung and/or colorectal cancers.

The present disclosure also provides methods of treating cancer, in particular non-small cell lung and/or colorectal cancers, by administering a therapeutically effective amount of any one or a combination of the solid state forms of AMG-510 of the present disclosure, or at least one of the above pharmaceutical compositions, to a subject suffering from non-small cell lung and/or colorectal cancers, or otherwise in need of the treatment.

The present disclosure also provides uses of the solid state forms of AMG-510 of the present disclosure, or at least one of the above pharmaceutical compositions, for the manufacture of medicaments for treating cancer e.g., non-small cell lung and/or colorectal cancers.

BRIEF DESCRIPTION OF THE DRAWINGS

FIG. 1 shows a characteristic X-ray powder diffraction pattern (XRPD) of AMG-510 amorphous.

FIG. 2 shows a XRPD of AMG-510 Form 1.

FIG. 3 shows a XRPD of AMG-510 Form 2.

FIG. 4 shows a XRPD of AMG-510 Form A.

FIG. 5 shows a XRPD of AMG-510 Form B.

FIG. 6 shows a XRPD of AMG-510 Form H1.

FIG. 7 shows a XRPD of AMG-510 Form H2.

FIG. 8 shows a XRPD of AMG-510 Form 3.

FIG. 9 shows a XRPD of AMG-510 Form H3.

FIG. 10 shows a XRPD of AMG-510: succinic acid Form 51.

FIG. 11 shows a XRPD of AMG-510 Form C1.

FIG. 12 shows a XRPD of AMG-510 Form C2.

FIG. 13 shows a XRPD of AMG-510 Form C3.

FIG. 14 shows a XRPD of AMG-510 Form C4.

FIG. 15 shows a XRPD of AMG-510 Form H4.

FIG. 16 shows a XRPD of AMG-510 Form D.

FIG. 17 shows a XRPD of AMG-510 Form 4 (Example 19).

FIG. 18 shows a XRPD of AMG-510 Form 4. (Example 20)

FIG. 19. $^{13}C$ NMR spectrum of AMG-510, Form 4

DETAILED DESCRIPTION OF THE DISCLOSURE

The present disclosure encompasses solid state forms of AMG-510, including crystalline polymorphs of AMG-510, crystalline polymorphs of AMG-510 salts, cocrystals of AMG-510, processes for preparation thereof, and pharmaceutical compositions thereof.

Solid state properties of AMG-510 and crystalline polymorphs thereof can be influenced by controlling the conditions under which AMG-510 and crystalline polymorphs thereof are obtained in solid form.

A solid state form (or polymorph) may be referred to herein as polymorphically pure or as substantially free of any other solid state (or polymorphic) forms. As used herein in this context, the expression "substantially free of any other forms" will be understood to mean that the solid state form contains about 20% (w/w) or less, about 10% (w/w) or less, about 5% (w/w) or less, about 2% (w/w) or less, about 1% (w/w) or less, or about 0% of any other forms of the subject compound as measured, for example, by XRPD. Thus, a crystalline polymorph of AMG-510 described herein as substantially free of any other solid state forms would be understood to contain greater than about 80% (w/w), greater than about 90% (w/w), greater than about 95% (w/w), greater than about 98% (w/w), greater than about 99% (w/w), or about 100% of the subject crystalline polymorph of AMG-510. In some embodiments of the disclosure, the described crystalline polymorph of AMG-510 may contain from about 1% to about 20% (w/w), from about 5% to about 20% (w/w), or from about 5% to about 10% (w/w) of one or more other crystalline polymorph of the same AMG-510.

Depending on which other crystalline polymorphs a comparison is made, the crystalline polymorphs of AMG-510 of the present disclosure may have advantageous properties selected from at least one of the following: chemical purity, flowability, solubility, dissolution rate, morphology or crystal habit, stability, such as chemical stability as well as thermal and mechanical stability with respect to polymorphic conversion, stability towards dehydration and/or storage stability, low content of residual solvent, a lower degree of hygroscopicity, flowability, and advantageous processing and handling characteristics such as compressibility and bulk density.

A solid state form, such as a crystal form or an amorphous form, may be referred to herein as being characterized by graphical data "as depicted in" or "as substantially depicted in" a Figure. Such data include, for example, powder X-ray diffractograms and solid state NMR spectra. As is well-known in the art, the graphical data potentially provides additional technical information to further define the respective solid state form (a so-called "fingerprint") which cannot necessarily be described by reference to numerical values or peak positions alone. In any event, the skilled person will understand that such graphical representations of data may be subject to small variations, e.g., in peak relative intensities and peak positions due to certain factors such as, but not limited to, variations in instrument response and variations in sample concentration and purity, which are well known to the skilled person. Nonetheless, the skilled person would readily be capable of comparing the graphical data in the Figures herein with graphical data generated for an unknown crystal form and confirm whether the two sets of graphical data are characterizing the same crystal form or two different crystal forms. A crystal form of AMG-510 referred to herein as being characterized by graphical data "as depicted in" or "as substantially depicted in" a Figure will thus be understood to include any crystal forms of AMG-510 characterized with the graphical data having such small variations, as are well known to the skilled person, in comparison with the Figure.

As used herein, crystalline AMG-510: succinic acid is a distinct molecular species. Crystalline AMG-510: succinic acid may be a co-crystal of AMG-510 and succinic acid. Alternatively crystalline AMG-510: succinic acid may be a salt.

"Co-Crystal" or "Cocrystal" as used herein is defined as a crystalline material including two or more molecules in the same crystalline lattice and associated by non-ionic and non-covalent bonds. In some embodiments, the cocrystal includes two molecules which are in natural state.

"Cocrystal former" or "crystal former" as used herein is defined as a molecule that forms a cocrystal with AMG-510 or salts thereof, for example succinic acid.

As used herein, solid state forms of AMG-510 relates to solid state forms of AMG-510 and AMG-510 salts and include co-crystal forms of AMG-510 (and salts thereof) and a crystal former. As used herein, and unless stated otherwise, the term "anhydrous" in relation to crystalline forms of AMG-510, relates to a crystalline form of AMG-510 which does not include any crystalline water (or other solvents) in a defined, stoichiometric amount within the crystal. Moreover, unless otherwise indicated, an "anhydrous" form would generally not contain more than 1% (w/w), of either water or organic solvents as measured for example by TGA.

The term "solvate," as used herein and unless indicated otherwise, refers to a crystal form that incorporates a solvent in the crystal structure. When the solvent is water, the solvate is often referred to as a "hydrate." The solvent in a solvate may be present in either a stoichiometric or in a non-stoichiometric amount.

As used herein, the term "isolated" in reference to crystalline polymorph of AMG-510 of the present disclosure corresponds to a crystalline polymorph of AMG-510 that is physically separated from the reaction mixture in which it is formed.

As used herein, unless stated otherwise, the XRPD measurements are taken using copper Kα radiation wavelength 1.54184 Å. XRPD peaks reported herein are measured using CuK α radiation, λ=1.54184 Å, typically at a temperature of 25±3° C.

A thing, e.g., a reaction mixture, may be characterized herein as being at, or allowed to come to "room temperature" or "ambient temperature", often abbreviated as "RT." This means that the temperature of the thing is close to, or the same as, that of the space, e.g., the room or fume hood, in which the thing is located. Typically, room temperature is from about 20° C. to about 30° C., or about 22° C. to about 27° C., or about 25° C.

The amount of solvent employed in a chemical process, e.g., a reaction or crystallization, may be referred to herein as a number of "volumes" or "vol" or "V." For example, a material may be referred to as being suspended in 10 volumes (or 10 vol or 10V) of a solvent. In this context, this expression would be understood to mean milliliters of the solvent per gram of the material being suspended, such that suspending a 5 grams of a material in 10 volumes of a solvent means that the solvent is used in an amount of 10 milliliters of the solvent per gram of the material that is being suspended or, in this example, 50 mL of the solvent. In another context, the term "v/v" may be used to indicate the number of volumes of a solvent that are added to a liquid mixture based on the volume of that mixture. For example, adding solvent X (1.5 v/v) to a 100 ml reaction mixture would indicate that 150 mL of solvent X was added.

A process or step may be referred to herein as being carried out "overnight." This refers to a time interval, e.g., for the process or step, that spans the time during the night, when that process or step may not be actively observed. This time interval is from about 8 to about 20 hours, or about 10-18 hours, in some cases about 16 hours.

As used herein, the term "reduced pressure" refers to a pressure that is less than atmospheric pressure. For example, reduced pressure is about 10 mbar to about 50 mbar.

As used herein and unless indicated otherwise, the term "ambient conditions" refer to atmospheric pressure and a temperature of 22-24° C.

The present disclosure includes an amorphous form of AMG-510. The amorphous form of AMG-510 may be characterized by an X-ray powder diffraction pattern substantially as depicted in FIG. 1.

The present disclosure includes a crystalline polymorph of AMG-510, designated Form 1. The crystalline Form 1 of AMG-510 may be characterized by data selected from one or more of the following: an X-ray powder diffraction pattern substantially as depicted in FIG. 2; an X-ray powder diffraction pattern having peaks at 8.8, 10.8, 13.6, 14.2 and 19.0 degrees 2-theta±0.2 degrees 2-theta; and combinations of these data.

Crystalline Form 1 of AMG-510 may be further characterized by an X-ray powder diffraction pattern having peaks at 8.8, 10.8, 13.6, 14.2 and 19.0 degrees 2-theta±0.2 degrees 2-theta, and also having any one, two, three, four or five additional peaks selected from 12.0, 15.0, 18.0, 19.8 and 25.0 degrees 2-theta±0.2 degrees 2-theta.

Crystalline Form 1 of AMG-510 may be alternatively characterized by an X-ray powder diffraction pattern having peaks at 8.8, 10.8, 12.0, 13.6, 14.2, 15.0, 18.0, 19.0, 19.8, and 25.0 degrees 2-theta±0.2 degrees 2-theta.

In one embodiment of the present disclosure, crystalline Form 1 of AMG-510 is isolated.

Crystalline Form 1 of AMG-510 may be anhydrous form.

Crystalline Form 1 of AMG-510 may be characterized by each of the above characteristics alone or by all possible combinations, e.g., an XRPD pattern having peaks at 8.8, 10.8, 13.6, 14.2 and 19.0 degrees 2-theta±0.2 degrees 2-theta; an XRPD pattern as depicted in FIG. 2, and combinations thereof.

The present disclosure includes a crystalline polymorph of AMG-510, designated Form 2. The crystalline Form 2 of AMG-510 may be characterized by data selected from one or more of the following: an X-ray powder diffraction pattern substantially as depicted in FIG. 3; an X-ray powder diffraction pattern having peaks at 7.4, 11.3, 14.7, 17.2 and 18.4 degrees 2-theta±0.2 degrees 2-theta; and combinations of these data.

Crystalline Form 2 of AMG-510 may be further characterized by an X-ray powder diffraction pattern having peaks at 7.4, 11.3, 14.7, 17.2 and 18.4 degrees 2-theta±0.2 degrees 2-theta, and also having any one, two, three, four or five additional peaks selected from 9.9, 10.1, 10.4, 13.3 and 24.3 degrees 2-theta±0.2 degrees 2-theta.

Crystalline Form 2 of AMG-510 may be alternatively characterized by an X-ray powder diffraction pattern having peaks at 7.4, 9.9, 10.1, 10.4, 11.3, 13.3, 14.7, 17.2, 18.4, 24.3 degrees 2-theta±0.2 degrees 2-theta.

In one embodiment of the present disclosure, crystalline Form 2 of AMG-510 is isolated.

Crystalline Form 2 of AMG-510 may be anhydrous form or solvated form.

Crystalline Form 2 of AMG-510 may be anhydrous form or methanol solvate.

Crystalline Form 2 of AMG-510 may be characterized by each of the above characteristics alone or by all possible combinations, e.g., an XRPD pattern having peaks at 7.4, 11.3, 14.7, 17.2 and 18.4 degrees 2-theta±0.2 degrees 2-theta; an XRPD pattern as depicted in FIG. 3, and combinations thereof.

The present disclosure includes a crystalline polymorph of AMG-510, designated Form A. The crystalline Form A of AMG-510 may be characterized by data selected from one or more of the following: an X-ray powder diffraction pattern substantially as depicted in FIG. 4; an X-ray powder diffraction pattern having peaks at 17.0, 19.0, 21.8, and 22.8 degrees 2-theta±0.2 degrees 2-theta; and combinations of these data.

Crystalline Form A of AMG-510 may be further characterized by an X-ray powder diffraction pattern having peaks at 17.0, 19.0, 21.8, and 22.8 degrees 2-theta±0.2 degrees 2-theta, and also having any one, two, three, four or five additional peaks selected from 11.8, 14.5, 20.1 and 23.7 degrees 2-theta±0.2 degrees 2-theta.

Crystalline Form A of AMG-510 may be alternatively characterized by an X-ray powder diffraction pattern having peaks at 11.8, 14.5, 17.0, 19.0, 21.8, 20.1, 22.8, and 23.7 degrees 2-theta±0.2 degrees 2-theta.

In one embodiment of the present disclosure, crystalline Form A of AMG-510 is isolated.

Crystalline Form A of AMG-510 may be a solvated form. Crystalline Form A of AMG-510 may be an acetonitrile solvate.

Crystalline Form A of AMG-510 may be characterized by each of the above characteristics alone or by all possible combinations, e.g., an XRPD pattern having peaks at 17.0, 19.0, 21.8, and 22.8 degrees 2-theta±0.2 degrees 2-theta; an XRPD pattern as depicted in FIG. 4, and combinations thereof.

The present disclosure includes a crystalline polymorph of AMG-510, designated Form B. The crystalline Form B of AMG-510 may be characterized by data selected from one or more of the following: an X-ray powder diffraction pattern substantially as depicted in FIG. 5; an X-ray powder diffraction pattern having peaks at 7.1, 9.4, 16.8, 17.8 and 22.8 degrees 2-theta±0.2 degrees 2-theta; and combinations of these data.

Crystalline Form B of AMG-510 may be further characterized by an X-ray powder diffraction pattern having peaks at 7.1, 9.4, 16.8, 17.8 and 22.8 degrees 2-theta±0.2 degrees 2-theta, and also having any one, two, three, four or five additional peaks selected from 10.1, 10.9, 14.3, 19.1 and 20.2 degrees 2-theta±0.2 degrees 2-theta.

Crystalline Form B of AMG-510 may be alternatively characterized by an X-ray powder diffraction pattern having peaks at 7.1, 9.4, 10.1, 10.9, 14.3, 16.8, 17.8, 19.1, 20.2, and 22.8 degrees 2-theta±0.2 degrees 2-theta.

In one embodiment of the present disclosure, crystalline Form B of AMG-510 is isolated.

Crystalline Form B of AMG-510 may be a solvated form. Crystalline Form B of AMG-510 may be a dichloromethane solvate.

Crystalline Form B of AMG-510 may be characterized by each of the above characteristics alone or by all possible combinations, e.g., an XRPD pattern having peaks at 7.1, 9.4, 16.8, 17.8 and 22.8 degrees 2-theta±0.2 degrees 2-theta; an XRPD pattern as depicted in FIG. 5, and combinations thereof.

The present disclosure includes a crystalline polymorph of AMG-510, designated Form H1. The crystalline Form H1 of AMG-510 may be characterized by data selected from one or more of the following: an X-ray powder diffraction pattern substantially as depicted in FIG. 6; an X-ray powder diffraction pattern having peaks at 10.1, 16.8, 19.6 and 25.5 degrees 2-theta±0.2 degrees 2-theta; and combinations of these data.

Crystalline Form H1 of AMG-510 may be further characterized by an X-ray powder diffraction pattern having peaks at 10.1, 16.8, 19.6 and 25.5 degrees 2-theta±0.2 degrees 2-theta, and also having any one, two, three, four, five or six additional peaks selected from 8.9, 9.5, 14.1, 18.1, 19.1 and 21.6 degrees 2-theta±0.2 degrees 2-theta.

Crystalline Form H1 of AMG-510 may be further characterized by an X-ray powder diffraction pattern having peaks at 8.9, 9.5, 10.1, 14.1, 16.8, 18.1, 19.1, 19.6, 25.5, and 21.6 degrees 2-theta±0.2 degrees 2-theta.

In one embodiment of the present disclosure, crystalline Form H1 of AMG-510 is isolated.

Crystalline Form H1 of AMG-510 may be a hydrate form.

Crystalline Form H1 of AMG-510 may be characterized by each of the above characteristics alone or by all possible combinations, e.g., an XRPD pattern having peaks at 10.1, 16.8, 19.6 and 25.5 degrees 2-theta±0.2 degrees 2-theta; an XRPD pattern as depicted in FIG. 6, and combinations thereof.

The present disclosure includes a crystalline polymorph of AMG-510, designated Form H2. The crystalline Form H2 of AMG-510 may be characterized by data selected from one or more of the following: an X-ray powder diffraction pattern substantially as depicted in FIG. 7; an X-ray powder diffraction pattern having peaks at 6.0, 7.5, 10.1, 16.8, 19.6 and 25.5 degrees 2-theta±0.2 degrees 2-theta; and combinations of these data.

Crystalline Form H2 of AMG-510 may be further characterized by an X-ray powder diffraction pattern having peaks at 6.0, 7.5, 10.1, 16.8, 19.6 and 25.5 degrees 2-theta±0.2 degrees 2-theta, and also having any one, two, three, four, five or six additional peaks selected from 8.9, 9.5, 14.1, 18.1, 19.1 and 21.6 degrees 2-theta±0.2 degrees 2-theta.

Crystalline Form H2 of AMG-510 may be further characterized by an X-ray powder diffraction pattern having peaks at 6.0, 7.5, 8.9, 9.5, 10.1, 14.1, 16.8, 18.1, 19.1, 19.6, and 25.5 degrees 2-theta±0.2 degrees 2-theta.

In one embodiment of the present disclosure, crystalline Form H2 of AMG-510 is isolated.

Crystalline Form H2 of AMG-510 may be a hydrate form.

Crystalline Form H2 of AMG-510 may be characterized by each of the above characteristics alone or by all possible combinations, e.g., an XRPD pattern having peaks at 6.0, 7.5, 10.1, 16.8, 19.6 and 25.5 degrees 2-theta±0.2 degrees 2-theta; an XRPD pattern as depicted in FIG. 7, and combinations thereof.

The present disclosure includes a crystalline polymorph of AMG-510, designated Form 3. The crystalline Form 3 of AMG-510 may be characterized by data selected from one or more of the following: an X-ray powder diffraction pattern substantially as depicted in FIG. 8; an X-ray powder diffraction pattern having peaks at 6.3, 8.4, 9.5, 16.0 and 17.6 degrees 2-theta±0.2 degrees 2-theta; and combinations of these data.

Crystalline Form 3 of AMG-510 may be further characterized by an X-ray powder diffraction pattern having peaks at 6.3, 8.4, 9.5, 16.0 and 17.6 degrees 2-theta±0.2 degrees 2-theta, and also having any one, two, three, four or five additional peaks selected from 10.4, 16.6, 18.8, 20.0 and 28.7 degrees 2-theta±0.2 degrees 2-theta.

Crystalline Form 3 of AMG-510 may be further characterized by an X-ray powder diffraction pattern having peaks at 6.3, 8.4, 9.5, 10.4, 16.0, 16.6, 17.6, 18.8, 20.0 and 28.7 degrees 2-theta±0.2 degrees 2-theta.

In one embodiment of the present disclosure, crystalline Form 3 of AMG-510 is isolated.

In one embodiment of the present disclosure, crystalline Form 3 of AMG-510 may be an anhydrous form.

Crystalline Form 3 of AMG-510 may be characterized by each of the above characteristics alone or by all possible combinations, e.g., an XRPD pattern having peaks at 6.3, 8.4, 9.5, 16.0 and 17.6 degrees 2-theta±0.2 degrees 2-theta; an XRPD pattern as depicted in FIG. 8, and combinations thereof.

The present disclosure includes a crystalline polymorph of AMG-510, designated Form H3. The crystalline Form H3 of AMG-510 may be characterized by data selected from one or more of the following: an X-ray powder diffraction pattern substantially as depicted in FIG. 9; an X-ray powder diffraction pattern having peaks at 5.4, 7.3, 18.1, 19.8 and 20.4 degrees 2-theta±0.2 degrees 2-theta; and combinations of these data.

Crystalline Form H3 of AMG-510 may be further characterized by an X-ray powder diffraction pattern having peaks at 5.4, 7.3, 18.1, 19.8 and 20.4 degrees 2-theta±0.2 degrees 2-theta, and also having any one, two, three, four or five additional peaks selected from 14.5, 16.0, 16.6, 21.7 and 24.8 degrees 2-theta±0.2 degrees 2-theta.

Crystalline Form H3 of AMG-510 may be further characterized by an X-ray powder diffraction pattern having peaks at 5.4, 7.3, 14.5, 16.0, 16.6, 18.1, 19.8, 20.4, 21.7, and 24.8 degrees 2-theta±0.2 degrees 2-theta.

In one embodiment of the present disclosure, crystalline Form H3 of AMG-510 is isolated.

In one embodiment of the present disclosure, crystalline Form H3 of AMG-510 may be a hydrate form.

Crystalline Form H3 of AMG-510 may be characterized by each of the above characteristics alone or by all possible combinations, e.g., an XRPD pattern having peaks at 5.4, 7.3, 18.1, 19.8 and 20.4 degrees 2-theta±0.2 degrees 2-theta; an XRPD pattern as depicted in FIG. 9, and combinations thereof.

The present disclosure further encompasses crystalline AMG-510: succinic acid. Crystalline AMG-510: succinic acid may be a co-crystal of AMG-510 and succinic acid. Alternatively, crystalline AMG-510: succinic acid may be a salt, i.e., AMG-510 succinate. AMG-510 succinate may be in a ratio between about 1:1 to about 1:2 of AMG-510 and succinic acid. In one embodiment, AMG-510 succinate may be in a 1:1 ratio of AMG-510 and succinic acid.

The present disclosure includes a crystalline polymorph of AMG-510: succinic acid, designated Form S1. The crystalline Form S1 of AMG-510: succinic acid may be characterized by data selected from one or more of the following: an X-ray powder diffraction pattern substantially as depicted in FIG. 10; an X-ray powder diffraction pattern having peaks at 11.0, 14.5, 22.0, 23.2 and 26.0 degrees 2-theta±0.2 degrees 2-theta; and combinations of these data.

Crystalline Form S1 of AMG-510: succinic acid may be further characterized by an X-ray powder diffraction pattern having peaks at 11.0, 14.5, 22.0, 23.2 and 26.0 degrees 2-theta±0.2 degrees 2-theta, and also having any one, two, three or four additional peaks selected from 9.5, 17.2, 18.9 and 27.3 degrees 2-theta±0.2 degrees 2-theta.

Crystalline Form S1 of AMG-510: succinic acid may be further characterized by an X-ray powder diffraction pattern having peaks at 9.5, 11.0, 14.5, 17.2, 18.9, 22.0, 23.2, 26.0, 27.3 degrees 2-theta±0.2 degrees 2-theta.

In one embodiment of the present disclosure, crystalline Form S1 of AMG-510: succinic acid is isolated.

In one embodiment of the present disclosure, crystalline Form S1 of AMG-510: succinic acid may be an anhydrous form.

Crystalline Form S1 of AMG-510: succinic acid may be characterized by each of the above characteristics alone or by all possible combinations, e.g., an XRPD pattern having peaks at 11.0, 14.5, 22.0, 23.2 and 26.0 degrees 2-theta±0.2 degrees 2-theta; an XRPD pattern as depicted in FIG. 10, and combinations thereof.

The present disclosure includes a crystalline polymorph of AMG-510, designated Form C. The crystalline Form C of AMG-510 may be characterized by data selected from one or more of the following: an X-ray powder diffraction pattern substantially as depicted in at least one of FIGS. 11-14; an X-ray powder diffraction pattern having peaks at 7.1, 9.0, 10.5, 14.1 and 16.6 degrees 2-theta±0.2 degrees 2-theta; and combinations of these data.

Crystalline Form C of AMG-510 may be further characterized by an X-ray powder diffraction pattern having peaks at 7.1, 9.0, 10.5, 14.1 and 16.6 degrees 2-theta±0.2 degrees 2-theta, and also having any one, two, three or four additional peaks selected from 9.8, 13.7, 17.4 and 21.3 degrees 2-theta±0.2 degrees 2-theta.

Crystalline Form C of AMG-510 may be further characterized by an X-ray powder diffraction pattern having peaks at 7.1, 9.0, 9.8, 10.5, 13.7, 14.1, 16.6, 17.4, and 21.3 degrees 2-theta±0.2 degrees 2-theta.

In one embodiment of the present disclosure, crystalline Form C of AMG-510 is isolated.

In one embodiment of the present disclosure, crystalline Form C of AMG-510 may be a solvate form. Crystalline Form C of AMG-510 may be for example 2-propanol solvate (nominated Form C1), acetone solvate (nominated Form C2), tetrahydrofuran solvate (nominated Form C3) and methyl ethyl ketone solvate (nominated Form C4).

Crystalline Form C of AMG-510 may be characterized by each of the above characteristics alone or by all possible combinations, e.g., an XRPD pattern having peaks at 7.1, 9.0, 10.5, 14.1 and 16.6 degrees 2-theta±0.2 degrees 2-theta; an XRPD pattern as depicted in at least one of FIGS. 11-14, and combinations thereof.

The present disclosure includes a crystalline polymorph of AMG-510, designated Form H4. The crystalline Form H4 of AMG-510 may be characterized by data selected from one or more of the following: an X-ray powder diffraction pattern substantially as depicted in FIG. 15; an X-ray powder diffraction pattern having peaks at 5.8, 7.7, 11.5, 12.0 and 19.1 degrees 2-theta±0.2 degrees 2-theta; and combinations of these data.

Crystalline Form H4 of AMG-510 may be further characterized by an X-ray powder diffraction pattern having peaks at 5.8, 7.7, 11.5, 12.0 and 19.1 degrees 2-theta±0.2 degrees 2-theta, and also having any one, two, three, four or five additional peaks selected from 14.3, 16.1, 18.3, 21.8 and 24.0 degrees 2-theta±0.2 degrees 2-theta.

Crystalline Form H4 of AMG-510 may be further characterized by an X-ray powder diffraction pattern having peaks at 5.8, 7.7, 11.5, 12.0, 14.3, 16.1, 18.3, 19.1, 21.8 and 24.0 degrees 2-theta±0.2 degrees 2-theta.

In one embodiment of the present disclosure, crystalline Form H4 of AMG-510 is isolated.

In one embodiment of the present disclosure, crystalline Form H4 of AMG-510 may be a hydrate form.

Crystalline Form H4 of AMG-510 may be characterized by each of the above characteristics alone or by all possible combinations, e.g., an XRPD pattern having peaks at 5.8, 7.7, 11.5, 12.0 and 19.1 degrees 2-theta±0.2 degrees 2-theta; an XRPD pattern as depicted in FIG. 15, and combinations thereof.

The present disclosure includes a crystalline polymorph of AMG-510, designated Form D. The crystalline Form D of AMG-510 may be characterized by data selected from one or more of the following: an X-ray powder diffraction pattern substantially as depicted in FIG. 16; an X-ray powder diffraction pattern having peaks at 6.9, 8.2, 11.5, 17.3 and 18.3 degrees 2-theta±0.2 degrees 2-theta; and combinations of these data.

Crystalline Form D of AMG-510 may be further characterized by an X-ray powder diffraction pattern having peaks at 6.9, 8.2, 11.5, 17.3 and 18.3 degrees 2-theta±0.2 degrees 2-theta, and also having any one, two, three or four additional peaks selected from 9.7, 12.4, 15.1, and 20.9 degrees 2-theta±0.2 degrees 2-theta.

Crystalline Form D of AMG-510 may be further characterized by an X-ray powder diffraction pattern having peaks at 6.9, 8.2, 9.7, 11.5, 12.4, 15.1, 17.3, 18.3, and 20.9 degrees 2-theta±0.2 degrees 2-theta.

In one embodiment of the present disclosure, crystalline Form D of AMG-510 is isolated.

Crystalline Form D of AMG-510 may be a solvated form. Crystalline Form D of AMG-510 may be an ethanol solvate or a hydrate. Particularly, Form D of AMG-510 may be a hydrate.

Crystalline Form D of AMG-510 may be characterized by each of the above characteristics alone or by all possible combinations, e.g., an XRPD pattern having peaks at 6.9, 8.2, 11.5, 17.3 and 18.3 degrees 2-theta±0.2 degrees 2-theta; an XRPD pattern as depicted in FIG. 16, and combinations thereof.

The present disclosure includes a crystalline polymorph of AMG-510, designated Form 4. The crystalline Form 4 of AMG-510 may be characterized by data selected from one or more of the following: an X-ray powder diffraction pattern substantially as depicted in FIG. 17; an X-ray powder diffraction pattern having peaks at 12.6, 13.8, 14.8, 17.6 and 22.6 degrees 2-theta±0.2 degrees 2-theta; and combinations of these data.

Crystalline Form 4 of AMG-510 may be further characterized by an X-ray powder diffraction pattern having peaks at 12.6, 13.8, 14.8, 17.6 and 22.6 degrees 2-theta±0.2 degrees 2-theta, and also having any one, two, three, four or five additional peaks selected from 6.3, 8.3, 9.4, 18.0 and 25.1 degrees 2-theta±0.2 degrees 2-theta. Crystalline Form 4 of AMG-510 may be further characterized by an X-ray powder diffraction pattern having peaks at 12.6, 13.8, 14.8, 17.6 and 22.6 degrees 2-theta±0.2 degrees 2-theta, and also having any one, two, three, four or five additional peaks selected from 6.3, 8.3, 9.4, 18.0 and 25.1 degrees 2-theta±0.2 degrees 2-theta, as well as having any one peak at: 7.4, 10.0, 11.3, 11.5, 17.1 degrees 2-theta±0.2 degrees 2-theta.

Alternatively, crystalline Form 4 of AMG-510 may be further characterized by an X-ray powder diffraction pattern having peaks at 6.3, 8.3, 9.4, 12.6, 13.8, 14.8, 17.6, 18.0, 22.6, and 25.1 degrees 2-theta±0.2 degrees 2-theta. Alternatively, crystalline Form 4 of AMG-510 may be further characterized by an X-ray powder diffraction pattern having peaks at 6.3, 8.3, 9.4, 12.6, 13.8, 14.8, 17.6, 18.0, 22.6, and 25.1 degrees 2-theta±0.2 degrees 2-theta., and any one peak at: 7.4, 10.0, 11.3, 11.5, 17.1 degrees 2-theta±0.2 degrees 2-theta.

Crystalline Form 4 of AMG-510 may be alternatively characterized by an X-ray powder diffraction pattern having peaks at 12.6, 13.8, 14.8, 17.6 and 22.6 degrees 2-theta±0.2 degrees 2-theta, and also having any one, two, three, four or five additional peaks selected from 7.4, 10.0, 11.3, 11.5, 17.1 degrees 2-theta±0.2 degrees 2-theta.

Crystalline Form 4 of AMG-510 may be alternatively characterized by an X-ray powder diffraction pattern having peaks at 7.4, 10.0, 11.3, 11.5, 12.6, 13.8, 14.8, 17.1, 17.6 and 22.6 degrees 2-theta±0.2 degrees 2-theta.

Crystalline Form 4 of AMG-510 may be defined as described in any aspect or embodiment disclosed herein, and additionally by the absence of a peak at any one of 8.8, 9.0, 10.4, 10.8, 18.7, and 19.8 degrees 2-theta±0.2 degrees 2-theta. Particularly, crystalline Form 4 of AMG-510 may be defined as described in any aspect or embodiment disclosed herein, and additionally by the absence of a peak at any one of 8.8, 9.0, 10.4, 10.8, and 19.8 degrees 2-theta±0.2 degrees 2-theta.

Crystalline Form 4 of AMG-510 may be defined as described in any aspect or embodiment disclosed herein, and additionally by the absence of a peak at any one or more of 8.8, 9.0, 10.4, 10.8, 18.7, and 19.8 degrees 2-theta±0.2 degrees 2-theta. Particularly, crystalline Form 4 of AMG-510 may be defined as described in any aspect or embodiment disclosed herein, and additionally by the absence of peaks at 8.8, 9.0, 10.4, 10.8, 18.7, and 19.8 degrees 2-theta±0.2 degrees 2-theta.

Crystalline Form 4 of AMG-510 may be a characterized by a solid state $^{13}C$ NMR spectrum having signals at about 14.46, 30.10, 48.26, 121.27 and 135.42±0.2 ppm. Crystalline Form 4 of AMG-510 may be further characterized by a solid state $^{13}C$ NMR spectrum having the following chemical shift absolute differences from a peak at 42.45 ppm±1 ppm of: 27.99, 12.35, 5.81, 78.82 and 92.97 ppm±0.1 ppm. Crystalline Form 4 of AMG-510 may be a characterized by a solid state by a solid state $^{13}C$ NMR spectrum substantially as depicted in FIG. 19. Alternatively crystalline Form 4 of AMG-510 may be a characterized by the solid state $^{13}C$ NMR data in combination with the characteristic XRPD peaks as described in any of the aspects and embodiments disclosed herein.

Crystalline Form 4 of AMG-510 according to any aspect or embodiment described herein may be an anhydrous form, and thus does not contain water or organic solvents in the crystal structure. Crystalline Form 4 of AMG-510, as defined in any aspect or embodiment herein, may nevertheless include non-crystal bound water, preferably crystalline Form 4 of AMG-510 may contain: 2 wt % or less, 1.8 wt % or less, 1.6 wt % or less, 1.5 wt % or less, 1.2 wt % or less, 1 wt % or less, 0.75 wt % or less, 0.5 wt % or less, 0.25 wt % or less, or 0.1 wt % or less, of water or organic solvents.

In one embodiment of the present disclosure, crystalline Form 4 of AMG-510 is isolated.

Crystalline Form 4 of AMG-510, according to any aspect or embodiment described herein may be polymorphically pure, optionally containing no more than about 20%, no more than about 10%, no more than about 5%, no more than about 2%, no more than about 1%, or about 0% of any other solid state forms of AMG-510.

Crystalline Form 4 of AMG-510 may be characterized by each of the above characteristics alone or by all possible combinations, e.g., an XRPD pattern having peaks at 12.6, 13.8, 14.8, 17.6 and 22.6 degrees 2-theta±0.2 degrees 2-theta; an XRPD pattern as depicted in FIG. 17, and combinations thereof. The above solid state forms can be used to prepare other solid state forms of AMG-510, AMG-510 salts and their solid state forms.

The present disclosure encompasses a process for preparing Form 4 of AMG-510 as defined in any embodiment disclosed herein. The process comprises drying crystalline Form H3 as described in any embodiment disclosed herein, preferably under reduced pressure. The drying may be carried out at a temperature of: about 40° C. to about 140° C. about 50° C. to about 130° C., about 60° C. to about 120° C., about 70° C. to about 110° C., about 80° C. to about 105° C., about 85° C. to about 100° C., or about 90° C. to about 100° C. The drying may be conducted for a sufficient time to prepare Form 4, for example by monitoring using XRPD. Typically the drying is conducted over a period of about 1 hour to about 12 hours, about 2 hours to about 11 hours, about 4 hours to about 10 hours, about 6 hours to about 9 hours, or about 8 hours.

The present disclosure encompasses a process for preparing Form 4 of AMG-510 as defined in any embodiment disclosed herein. The process comprises suspending Form AMG-510 Form 2 as described in any embodiment disclosed herein, in water preferably at a temperature of about 10° C. to about 50° C., about 15° C. to about 40° C., about 20° C. to about 35° C., about 22° C. to about 30° C., about 22° C. to about 28° C., or about 24° C., or about room temperature. The mixture may be stirred for a sufficient time to prepare Form 4, for example by monitoring using XRPD. Typically, the suspension may be maintained for a period of about 30 minutes to about 72 hours, about 6 hours to about 48 hours, about 10 hours to about 36 hours, about 14 hours to about 24 hours, or about 16 hours ot about 20 hours, and optionally about 18 hours. The mixture may be filtered, and the solid dried. The drying is preferably carried out under reduced pressure. The drying may be carried out at a temperature of: about 40° C. to about 140° C. about 50° C. to about 130° C., about 60° C. to about 120° C., about 65° C. to about 110° C., about 70° C. to about 90° C., or about 80° C. Typically the drying is conducted over a period of about 1 hour to about 28 hours, about 4 hours to about 24 hours, about 10 hours to about 20 hours, about 14 hours to about 18 hours.

The present disclosure compasses a process for preparing Form H3 of AMG-510. The Form H3 as defined in any embodiment disclosed herein may be prepared by a process comprising suspending AMG-510 Form 2 in water. The mixture may be maintained at a temperature of about 10° C. to about 50° C., about 15° C. to about 40° C., about 20° C. to about 35° C., about 22° C. to about 30° C., about 22° C. to about 28° C., or about 24° C. The mixture may be maintained for a period of time sufficient to convert the Form 2 to Form H3, as monitored by XRPD. The mixture may be optionally stirred. Typically the mixture is maintained for a period of about 1 day to about 10 days, about 2 days to about 9 days, about 4 days to about 8 days, about 5 days to about 7 days, or about 6 days.

The present disclosure encompasses a process for preparing Form 2 of AMG-510. The Form 2 as defined in any embodiment disclosed herein may be prepared by a process comprising drying Form A or Form B of AMG-510 as defined in any embodiment, optionally at temperature of: about 300 to about 80° C., about 40° C. to about 70° C., about 45° C. to about 60° C., or about 50° C. The drying may be conducted for a sufficient time to prepare Form 4, for example by monitoring using XRPD. Typically the drying is conducted over a period of about 30 minutes to about 8 hours, about 1 hour to about 7 hours, about 2 hours to about 6 hours, about 3 hours to about 5 hours, or about 4 hours.

The present disclosure encompasses a further process for preparing Form 2 of AMG-510. The Form 2 as defined in any embodiment disclosed herein may also be prepared by a process comprising suspending amorphous form of AMG-510 in methanol. The mixture may be maintained at a temperature of about 10° C. to about 50° C., about 15° C. to about 40° C., about 20° C. to about 35° C., about 22° C. to about 30° C., about 22° C. to about 28° C., or about 25° C. The mixture may be maintained for a period of time sufficient to convert the amorphous form to Form H3, as monitored by XRPD. The mixture may be optionally stirred. Typically the mixture is maintained for a period of about 12 hours to about 9 days, about 1 day to about 8 days, about 1 day to about 6 days, about 2 days to about 5 days, or about 3 days. The suspension may be isolated by filtration, optionally by vacuum filtration. The product may be a methanol solvate, which can be dried to form AMG-Form 2. The drying may be carried out under reduced pressure. The drying may be carried out at a temperature of: about 30° C. to about 110° C. about 40° C. to about 100° C., about 45° C. to about 90° C., about 50° C. to about 80° C., about 55° C. to about 70° C., or about 55° C. to about 65° C., or about 60° C. The drying may be conducted for a sufficient time to prepare Form 2, for example by monitoring using XRPD. Typically the drying is conducted over a period of about 1 hour to about 10 hours, about 2 hours to about 8 hours, about 3 hours to about 7 hours, about 4 hours to about 6 hours, or about 5 hours.

The present disclosure encompasses a process for preparing Form A of AMG-510. Form A as described in any embodiment herein may be prepared by a process comprising suspending amorphous form of AMG-510 in acetonitrile. The mixture may be maintained at a temperature of about 10° C. to about 50° C., about 15° C. to about 40° C., about 20° C. to about 35° C., about 22° C. to about 30° C., about 22° C. to about 28° C., or about 25° C. The mixture may be maintained for a period of time sufficient to convert the amorphous form to Form A, as monitored by XRPD. The mixture may be optionally stirred. Typically the mixture is maintained for a period of about 12 hours to about 9 days, about 1 day to about 8 days, about 1 day to about 6 days, about 2 days to about 5 days, or about 3 days. The suspension may be isolated by filtration, optionally by vacuum filtration.

The present disclosure encompasses a process for preparing Form B of AMG-510. Form B as described in any embodiment herein may be prepared by a process comprising suspending amorphous form of AMG-510 in dichloromethane. The mixture may be maintained at a temperature of about 10° C. to about 50° C., about 15° C. to about 40° C., about 20° C. to about 35° C., about 22° C. to about 30° C., about 22° C. to about 28° C., or about 25° C. The mixture may be maintained for a period of time sufficient to convert the amorphous form to Form A, as monitored by XRPD. The mixture may be optionally stirred. Typically the mixture is maintained for a period of about 12 hours to about 9 days, about 1 day to about 8 days, about 1 day to about 6 days, about 2 days to about 5 days, or about 3 days. The suspension may be isolated by filtration, optionally by vacuum filtration.

The present disclosure encompasses a process for preparing amorphous form of AMG-510. Amorphous form of AMG-510 may be prepared by a process comprising preparing a solution of AMG-510 in ethyl acetate and removing the solvent. The solution may be prepared by dissolving AMG-510 in ethyl acetate, optionally at a temperature of about 40° C. to about 90° C., about 50° C. to about 85° C., about 60° C. to about 80° C., about 70° C. to about 78° C., or about 77° C. The mixture may be filtered, and the filtrate solution may be evaporated, for example on a rotary evaporator to obtain amorphous AMG-510.

The present disclosure encompasses a further process for preparing amorphous form of AMG-510. Amorphous form of AMG-510 may alternatively be prepared by a process comprising preparing a solution of AMG-510 in acetic acid, and removing the solvent. The solution may be prepared by dissolving AMG-510 in acid, optionally at a temperature of about 40° C. to about 90° C., about 50° C. to about 85° C., about 55° C. to about 80° C., about 60° C. to about 70° C., or about 63° C. The mixture may be allowed cooled to about 15° C. to about 38° C., about 20° C. to about 35° C., about 22° C. to about 30° C., about 22° C. to about 28° C., or about 25° C. The resulting solution may be evaporated, for example on a rotary evaporator to obtain amorphous AMG-510.

The present disclosure encompasses yet a further alternative process for preparing amorphous form of AMG-510. Amorphous form of AMG-510 may alternatively be prepared milling AMG-510. The milling may be conducted in a ball mill, preferably at a frequency of: about 100 rpm to about 1000 rpm, about 300 rpm to about 900 rpm, about 400 rpm to about 850 rpm, about 500 rpm to about 800 rpm, about 600 rpm to about 750 rpm, or about 700 rpm. Typically the milling is conducted over a period of time sufficient to form amorphous form of AMG-510, for example: about 30 minutes to about 6 hours, about 45 minutes to about 5 hours, about 1 hour to about 4 hours, about 1 hour to about 3 hours, or about 2 hours.

The present disclosure encompasses a process for preparing Form H2 of AMG-510. Form H2 as defined in any embodiment disclosed herein, may be prepared by a process comprising preparing a solution of AMG-510 in a mixture of acetone and water (preferably at a ratio of: about 3:1 to about 1:3, about 2:1 to about 1:2, about 1.5:1 to about 1:1.5, about 1.2:1 to about 1:1.2, or about 1:1), and cooling the solution. The solution may be prepared by dissolving AMG-510 in acetone/water, optionally at a temperature of about 40° C. to about 90° C., about 45° C. to about 80° C., about 50° C. to about 70° C., about 50° C. to about 65° C., or about 56° C., or at about reflux temperature. The solution may be filtered prior to being allowed to cool to about 15° C. to about 38° C., about 20° C. to about 35° C., about 22° C. to about 30° C., about 22° C. to about 28° C., or about 25° C.

The present disclosure encompasses a process for preparing Form H3 of AMG-510. Form H3 as described in any embodiment herein may be prepared by a process comprising suspending Form 2 of AMG-510 in water. The mixture may be maintained at a temperature of about 10° C. to about 50° C., about 15° C. to about 40° C., about 20° C. to about 35° C., about 22° C. to about 30° C., about 22° C. to about 28° C., or about 24° C. The mixture may be maintained for a period of time sufficient to convert the amorphous form to Form A, as monitored by XRPD. The mixture may be optionally stirred. Typically the mixture is maintained for a period of about 1 day to about 10 days, about 2 days to about 9 days, about 3 days to about 8 days, about 4 days to about 7 days, or about 6 days. The suspension may be isolated by filtration, optionally by vacuum filtration.

The present disclosure encompasses a process for preparing Form H4 of AMG-510. The present disclosure encompasses a process for preparing Form H4 of AMG-510 as defined in any embodiment disclosed herein. The process comprises drying crystalline Form H3 as described in any embodiment disclosed herein, preferably under reduced pressure. The drying may be carried out at temperature of: about 300 to about 90° C., about 35° C. to about 80° C., about 35° C. to about 60° C., about 35° C. to about 50° C., or about 35° C. to about 45°, or about 40° C. The drying may be conducted for a sufficient time to prepare Form H4, for example by monitoring using XRPD. Typically the drying is conducted over a period of about 30 minutes to about 8 hours, about 1 hour to about 7 hours, about 2 hours to about 6 hours, about 2 hours to about 5 hours, or about 3 hours.

The present disclosure encompasses a process for preparing AMG-510 succinate (i.e. a salt of AMG-510 with succinic acid). The process comprises precipitating or crystallizing a solution of AMG-510 and succinic acid a solvent. Preferably, succinic acid is used in an amount of about 0.5 mole equivalents. The solvent may be a ketone, particularly a $C_{3-6}$ ketone, particularly acetone, methylisobutylketone, or a mixture thereof. Preferably, the solvent is a mixture of acetone and methylisobutylketone, optionally in a volume ratio of about 5:1 to about 1:5, about 4:1 to about 1:4, about 3:1 to about 1:1, about 3:1 to about 2:1, about 3:1 to about 2.5:1, or about 2.7:1. The solution may be prepared by dissolving AMG-510 and succinic acid in the solvent (preferably acetone), optionally at a temperature of: about 380 to about 60° C., about 40° C. to about 55° C., about 45° C. to about 50° C., or at reflux temperature. The mixture may be cooled to about 20° C. to about 35° C., about 25° C. to about 35°, or about 30° C. Methylisobutylketone may be added to the solution, optionally at the same temperature of about 20° C. to about 35° C., about 25° C. to about 35°, or about 30° C. The mixture is preferably allowed to cool, optionally to about 20° C. to about 28° C., about 22° C. to about 26° C. The mixture may be concentrated to remove a portion of the solvent. The concentration may result in the formation of a suspension. Optionally methylisobutylketone is added to the suspension. The suspension may be maintained for a period of about 30 minutes to about 20 hours, about 2 hours to about 12 hours, about 6 hours to about 10 hours, about 6 hours to about 8 hours. The maintaining may be at a temperature about 20° C. to about 35° C., about 22° C. to about 30° C., about 22° C. to about 28° C., or about 24° C. The solid may be isolated, optionally by filtration, and optionally washed with the solvent (optionally acetone).

The present disclosure further encompasses a process according to any of the embodiments described above and herein, and further comprising combining the crystalline forms of AMG-510 or AMG-510 succinate with at least one pharmaceutically acceptable excipient to prepare a pharmaceutical composition or pharmaceutical formulation.

The present disclosure encompasses crystalline forms of AMG-510, or AMG-510 succinate, or a pharmaceutical composition or pharmaceutical composition which is obtainable by the processes described in any of the embodiments described above and herein.

The present disclosure encompasses a process for preparing other solid state forms of AMG-510, AMG-510 salts and their solid state forms thereof. The process includes preparing any one of the AMG-510 (salts) and solid state forms of AMG-510 by the processes of the present disclosure, and converting it to other AMG-510 salt(s).

The present disclosure provides the above described solid state forms of AMG-510 for use in the preparation of pharmaceutical compositions comprising AMG-510 and/or crystalline polymorphs thereof.

The present disclosure also encompasses the use of solid state forms of AMG-510 of the present disclosure for the preparation of pharmaceutical compositions of AMG-510 and/or crystalline polymorphs thereof. In particular the present disclosure encompasses the above described solid state forms of AMG-510 and salts thereof, for the preparation of a pharmaceutical composition or formulation, preferably an oral formulation in the form of a solid dispersion comprising AMG-510 or salt thereof.

The present disclosure includes processes for preparing the above mentioned pharmaceutical compositions. The processes include combining any one or a combination of the solid state forms of AMG-510 of the present disclosure with at least one pharmaceutically acceptable excipient.

The present disclosure further provides pharmaceutical compositions comprising the solid state forms of AMG-510 and salts thereof, or combinations thereof, according to the present disclosure.

Pharmaceutical combinations or formulations of the present disclosure contain any one or a combination of the solid state forms of AMG-510 of the present disclosure. In addition to the active ingredient, the pharmaceutical formulations of the present disclosure can contain one or more excipients. Excipients are added to the formulation for a variety of purposes.

Diluents increase the bulk of a solid pharmaceutical composition, and can make a pharmaceutical dosage form containing the composition easier for the patient and caregiver to handle. Diluents for solid compositions include, for example, microcrystalline cellulose (e.g. Avicel®), microfine cellulose, lactose, starch, pregelatinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g. Eudragit®), potassium chloride, powdered cellulose, sodium chloride, sorbitol, and talc.

Solid pharmaceutical compositions that are compacted into a dosage form, such as a tablet, can include excipients whose functions include helping to bind the active ingredient and other excipients together after compression. Binders for solid pharmaceutical compositions include acacia, alginic acid, carbomer (e.g. carbopol), carboxymethylcellulose sodium, dextrin, ethyl cellulose, gelatin, guar gum, hydrogenated vegetable oil, hydroxyethyl cellulose, hydroxypropyl cellulose (e.g. Klucel®), hydroxypropyl methyl cellulose (e.g. Methocel®), liquid glucose, magnesium aluminum silicate, maltodextrin, methylcellulose, polymethacrylates, povidone (e.g. Kollidon®, Plasdone®), pregelatinized starch, sodium alginate, and starch.

The dissolution rate of a compacted solid pharmaceutical composition in the patient's stomach can be increased by the addition of a disintegrant to the composition. Disintegrants include alginic acid, carboxymethylcellulose calcium, carboxymethylcellulose sodium (e.g. Ac-Di-Sol®, Primellose®), colloidal silicon dioxide, croscarmellose sodium, crospovidone (e.g. Kollidon®, Polyplasdone®), guar gum, magnesium aluminum silicate, methyl cellulose, microcrystalline cellulose, polacrilin potassium, powdered cellulose, pregelatinized starch, sodium alginate, sodium starch glycolate (e.g. Explotab®), and starch.

Glidants can be added to improve the flowability of a non-compacted solid composition and to improve the accuracy of dosing. Excipients that can function as glidants include colloidal silicon dioxide, magnesium trisilicate, powdered cellulose, starch, talc, and tribasic calcium phosphate.

When a dosage form such as a tablet is made by the compaction of a powdered composition, the composition is subjected to pressure from a punch and dye. Some excipients and active ingredients have a tendency to adhere to the surfaces of the punch and dye, which can cause the product to have pitting and other surface irregularities. A lubricant can be added to the composition to reduce adhesion and ease the release of the product from the dye. Lubricants include magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc, and zinc stearate.

Flavoring agents and flavor enhancers make the dosage form more palatable to the patient. Common flavoring agents and flavor enhancers for pharmaceutical products that can be included in the composition of the present disclosure include maltol, vanillin, ethyl vanillin, menthol, citric acid, fumaric acid, ethyl maltol, and tartaric acid.

Solid and liquid compositions can also be dyed using any pharmaceutically acceptable colorant to improve their appearance and/or facilitate patient identification of the product and unit dosage level.

In liquid pharmaceutical compositions of the present invention, AMG-510 and any other solid excipients can be dissolved or suspended in a liquid carrier such as water, vegetable oil, alcohol, polyethylene glycol, propylene glycol, or glycerin.

Liquid pharmaceutical compositions can contain emulsifying agents to disperse uniformly throughout the composition an active ingredient or other excipient that is not soluble in the liquid carrier. Emulsifying agents that can be useful in liquid compositions of the present invention include, for example, gelatin, egg yolk, casein, cholesterol, acacia, tragacanth, chondrus, pectin, methyl cellulose, carbomer, cetostearyl alcohol, and cetyl alcohol.

Liquid pharmaceutical compositions of the present invention can also contain a viscosity enhancing agent to improve the mouth-feel of the product and/or coat the lining of the gastrointestinal tract. Such agents include acacia, alginic acid bentonite, carbomer, carboxymethylcellulose calcium or sodium, cetostearyl alcohol, methyl cellulose, ethylcellulose, gelatin guar gum, hydroxyethyl cellulose, hydroxypropyl cellulose, hydroxypropyl methyl cellulose, maltodextrin, polyvinyl alcohol, povidone, propylene carbonate, propylene glycol alginate, sodium alginate, sodium starch glycolate, starch tragacanth, xanthan gum and combinations thereof.

Sweetening agents such as sorbitol, saccharin, sodium saccharin, sucrose, aspartame, fructose, mannitol, and invert sugar can be added to improve the taste.

Preservatives and chelating agents such as alcohol, sodium benzoate, butylated hydroxyl toluene, butylated hydroxyanisole, and ethylenediamine tetraacetic acid can be added at levels safe for ingestion to improve storage stability.

According to the present disclosure, a liquid composition can also contain a buffer such as gluconic acid, lactic acid, citric acid, or acetic acid, sodium gluconate, sodium lactate, sodium citrate, or sodium acetate. Selection of excipients and the amounts used can be readily determined by the formulation scientist based upon experience and consideration of standard procedures and reference works in the field.

The solid compositions of the present disclosure include powders, granulates, aggregates, and compacted compositions. The dosages include dosages suitable for oral, buccal, rectal, parenteral (including subcutaneous, intramuscular, and intravenous), inhalant, and ophthalmic administration. Although the most suitable administration in any given case will depend on the nature and severity of the condition being treated, in embodiments the route of administration is oral. The dosages can be conveniently presented in unit dosage form and prepared by any of the methods well-known in the pharmaceutical arts.

Dosage forms include solid dosage forms like tablets, powders, capsules, suppositories, sachets, troches, and lozenges, as well as liquid syrups, suspensions, and elixirs.

The dosage form of the present disclosure can be a capsule containing the composition, such as a powdered or granulated solid composition of the disclosure, within either a hard or soft shell. The shell can be made from gelatin and optionally contain a plasticizer such as glycerin and/or sorbitol, an opacifying agent and/or colorant.

The active ingredient and excipients can be formulated into compositions and dosage forms according to methods known in the art.

A composition for tableting or capsule filling can be prepared by wet granulation. In wet granulation, some or all of the active ingredients and excipients in powder form are blended and then further mixed in the presence of a liquid, typically water, that causes the powders to clump into granules. The granulate is screened and/or milled, dried, and then screened and/or milled to the desired particle size. The granulate can then be tableted, or other excipients can be added prior to tableting, such as a glidant and/or a lubricant.

A tableting composition can be prepared conventionally by dry blending. For example, the blended composition of the actives and excipients can be compacted into a slug or a sheet and then comminuted into compacted granules. The compacted granules can subsequently be compressed into a tablet.

As an alternative to dry granulation, a blended composition can be compressed directly into a compacted dosage form using direct compression techniques. Direct compression produces a more uniform tablet without granules. Excipients that are particularly well suited for direct compression tableting include microcrystalline cellulose, spray dried lactose, dicalcium phosphate dihydrate, and colloidal silica. The proper use of these and other excipients in direct compression tableting is known to those in the art with experience and skill in particular formulation challenges of direct compression tableting.

A capsule filling of the present disclosure can include any of the aforementioned blends and granulates that were described with reference to tableting, but they are not subjected to a final tableting step.

A pharmaceutical formulation of AMG-510 can be administered. AMG-510 may be formulated for administration to a mammal, in embodiments to a human, by injection. AMG-510 can be formulated, for example, as a viscous liquid solution or suspension, such as a clear solution, for injection. The formulation can contain one or more solvents. A suitable solvent can be selected by considering the solvent's physical and chemical stability at various pH levels, viscosity (which would allow for syringeability), fluidity, boiling point, miscibility, and purity. Suitable solvents include alcohol USP, benzyl alcohol NF, benzyl benzoate USP, and Castor oil USP. Additional substances can be added to the formulation such as buffers, solubilizers, and antioxidants, among others. Ansel et al., Pharmaceutical Dosage Forms and Drug Delivery Systems, 7th ed.

The solid state forms of AMG-510 and the pharmaceutical compositions and/or formulations of AMG-510 of the present disclosure can be used as medicaments, in embodiments in the treatment of cancer, in particular non-small cell lung cancer and/or colorectal cancers. In embodiments, the solid state forms of AMG-510 and the pharmaceutical compositions and/or formulations of the present disclosure may be used in the treatment of KRAS G12C-mutant tumours; particularly KRAS G12C-mutant solid tumours; particularly non-small-cell lung cancer, colorectal cancer, pancreatic cancer, appendiceal cancer, endometrial cancer, and melanoma; more particularly in the treatment of non-small-cell lung cancer or colorectal cancer; or in the treatment of advanced or metastatic non-small-cell lung cancer or colorectal cancer, and more particularly locally advanced or metastatic non-small-cell lung cancer or colorectal cancer, and especially in the treatment of advanced or metastatic non-small-cell lung cancer or colorectal cancer following at least one prior systemic therapy.

The present disclosure also provides methods of treating cancer, in particular non-small cell lung and/or colorectal cancers, by administering a therapeutically effective amount of any one or a combination of the solid state forms of AMG-510 of the present disclosure, or at least one of the above pharmaceutical compositions and/or formulations, to a subject in need of the treatment.

Aspect and embodiments of the present disclosure are set out in the below numbered clauses:

1. Amorphous form of AMG-510.

2. Amorphous form of AMG-510 according to Clause 1, characterized by an X-ray powder diffraction pattern substantially as depicted in FIG. 1.

3. Crystalline form of AMG-510, designated Form 1, which is characterized by data selected from one or more of the following:

(i) an X-ray powder diffraction pattern having peaks at 8.8, 10.8, 13.6, 14.2 and 19.0 degrees 2-theta±0.2 degrees 2-theta;

(ii) an X-ray powder diffraction pattern substantially as depicted in FIG. 2; and (iii) a combination of (i) and (ii).

4. Crystalline Form 1 of AMG-510 according to Clause 3, which is characterized by an X-ray powder diffraction pattern having peaks at 8.8, 10.8, 13.6, 14.2 and 19.0 degrees 2-theta±0.2 degrees 2-theta, and also having any one, two, three, four or five additional peaks selected from 12.0, 15.0, 18.0, 19.8 and 25.0 degrees 2-theta±0.2 degrees 2-theta.

5. Crystalline Form 1 of AMG-510 according to Clause 3 or Clause 4, which is characterized by an X-ray powder diffraction pattern having peaks at 8.8, 10.8, 12.0, 13.6, 14.2, 15.0, 18.0, 19.0, 19.8, and 25.0 degrees 2-theta±0.2 degrees 2-theta.

6. Crystalline Form 1 of AMG-510 according to any of Clauses 3, 4 or 5, which is an anhydrous form, optionally wherein the anhydrous form contains: 1 wt % or less, 0.75 wt % or less, 0.5 wt % or less, 0.25 wt % or less, or 0.1 wt % or less, of water or organic solvents.

7. A crystalline form of AMG-510, designated Form 2, which is characterized by data selected from one or more of the following:

(i) an X-ray powder diffraction pattern having peaks at 7.4, 11.3, 14.7, 17.2 and 18.4 degrees 2-theta±0.2 degrees 2-theta;

(ii) an X-ray powder diffraction pattern substantially as depicted in FIG. 3; and (iii) a combination of (i) and (ii).

8. Crystalline Form 2 of AMG-510 according to Clause 7, which is characterized by an X-ray powder diffraction pattern having peaks at 7.4, 11.3, 14.7, 17.2 and 18.4 degrees 2-theta±0.2 degrees 2-theta, and also having any one, two, three, four or five additional peaks selected from 9.9, 10.1, 10.4, 13.3 and 24.3 degrees 2-theta±0.2 degrees 2-theta.

9. Crystalline Form 2 of AMG-510 according to Clause 7 or Clause 8, which is characterized by an X-ray powder diffraction pattern having peaks at 7.4, 9.9, 10.1, 10.4, 11.3, 13.3, 14.7, 17.2, 18.4, 24.3 degrees 2-theta±0.2 degrees 2-theta.

10. Crystalline Form 2 of AMG-510 according to any of Clauses 7, 8 or 9, which is an anhydrous form, optionally wherein the anhydrous form contains: 1 wt % or less, 0.75 wt % or less, 0.5 wt % or less, 0.25 wt % or less, or 0.1 wt % or less, of water or organic solvents.

11. Crystalline Form 2 of AMG-510 according to any of Clauses 7, 8 or 9, which is a solvated form, optionally a methanol solvate.

12. A crystalline form of AMG-510, designated Form A, which is characterized by data selected from one or more of the following:

(i) an X-ray powder diffraction pattern having peaks at 17.0, 19.0, 21.8, and 22.8 degrees 2-theta±0.2 degrees 2-theta;

(ii) an X-ray powder diffraction pattern substantially as depicted in FIG. 4; and (iii) a combination of (i) and (ii).

13. Crystalline Form A of AMG-510 according to Clause 12, which is characterized by an X-ray powder diffraction pattern having peaks at 17.0, 19.0, 21.8, and 22.8 degrees 2-theta±0.2 degrees 2-theta, and also having any one, two, three, four or five additional peaks selected from 11.8, 14.5, 20.1 and 23.7 degrees 2-theta±0.2 degrees 2-theta.
14. Crystalline Form A of AMG-510 according to Clause 12 or Clause 13, which is characterized by an X-ray powder diffraction pattern having peaks at 11.8, 14.5, 17.0, 19.0, 21.8, 20.1, 22.8, and 23.7 degrees 2-theta±0.2 degrees 2-theta.
15. Crystalline Form 2 of AMG-510 according to any of Clauses 12, 13 or 14, which is a solvated form, optionally an acetonitrile solvate.
16. A crystalline form of AMG-510, designated Form B, which is characterized by data selected from one or more of the following:
 (i) an X-ray powder diffraction pattern having peaks at 7.1, 9.4, 16.8, 17.8 and 22.8 degrees 2-theta±0.2 degrees 2-theta;
 (ii) an X-ray powder diffraction pattern substantially as depicted in FIG. 5; and
 (iii) a combination of (i) and (ii).
17. Crystalline Form B of AMG-510 according to Clause 16, which is characterized by an X-ray powder diffraction pattern having peaks at 7.1, 9.4, 16.8, 17.8 and 22.8 degrees 2-theta±0.2 degrees 2-theta, and also having any one, two, three, four or five additional peaks selected from 10.1, 10.9, 14.3, 19.1 and 20.2 degrees 2-theta±0.2 degrees 2-theta.
18. Crystalline Form B of AMG-510 according to Clause 16 or Clause 17, which is characterized by an X-ray powder diffraction pattern having peaks at 7.1, 9.4, 10.1, 10.9, 14.3, 16.8, 17.8, 19.1, 20.2, and 22.8 degrees 2-theta±0.2 degrees 2-theta.
19. Crystalline Form B of AMG-510 according to any of Clauses 16, 17 or 18, which is a solvated form, optionally a dichloromethane solvate.
20. A crystalline form of AMG-510, designated Form H1, which is characterized by data selected from one or more of the following:
 (i) an X-ray powder diffraction pattern having peaks at 10.1, 16.8, 19.6 and 25.5 degrees 2-theta±0.2 degrees 2-theta;
 (ii) an X-ray powder diffraction pattern substantially as depicted in FIG. 6; and
 (iii) a combination of (i) and (ii).
21. Crystalline Form H1 of AMG-510 according to Clause 20, which is characterized by an X-ray powder diffraction pattern having peaks at 10.1, 16.8, 19.6 and 25.5 degrees 2-theta±0.2 degrees 2-theta, and also having any one, two, three, four, five or six additional peaks selected from 8.9, 9.5, 14.1, 18.1, 19.1 and 21.6 degrees 2-theta±0.2 degrees 2-theta.
22. Crystalline Form H1 of AMG-510 according to Clause 20 or Clause 21, which is characterized by an X-ray powder diffraction pattern having peaks at 8.9, 9.5, 10.1, 14.1, 16.8, 18.1, 19.1, 19.6, 25.5, and 21.6 degrees 2-theta 0.2 degrees 2-theta.
23. Crystalline Form H1 of AMG-510 according to any of Clauses 20, 21 or 22, which is a hydrate form, optionally a monohydrate.
24. A crystalline form of AMG-510, designated Form H2, which is characterized by data selected from one or more of the following:
 (i) an X-ray powder diffraction pattern having peaks at 6.0, 7.5, 10.1, 16.8, 19.6 and 25.5 degrees 2-theta±0.2 degrees 2-theta;
 (ii) an X-ray powder diffraction pattern substantially as depicted in FIG. 7; and
 (iii) a combination of (i) and (ii).
25. Crystalline Form H2 of AMG-510 according to Clause 24, which is characterized by an X-ray powder diffraction pattern having peaks at 6.0, 7.5, 10.1, 16.8, 19.6 and 25.5 degrees 2-theta±0.2 degrees 2-theta, and also having any one, two, three, four, five or six additional peaks selected from 8.9, 9.5, 14.1, 18.1, 19.1 and 21.6 degrees 2-theta±0.2 degrees 2-theta.
26. Crystalline Form H2 of AMG-510 according to Clause 24 or Clause 25, which is characterized by an X-ray powder diffraction pattern having peaks at 6.0, 7.5, 8.9, 9.5, 10.1, 14.1, 16.8, 18.1, 19.1, 19.6, and 25.5 degrees 2-theta±0.2 degrees 2-theta.
27. Crystalline Form H2 of AMG-510 according to any of Clauses 24, 25 or 26, which is a hydrate form.
28. A crystalline form of AMG-510, designated Form 3, which is characterized by data selected from one or more of the following:
 (i) an X-ray powder diffraction pattern having peaks at 6.3, 8.4, 9.5, 16.0 and 17.6 degrees 2-theta±0.2 degrees 2-theta;
 (ii) an X-ray powder diffraction pattern substantially as depicted in FIG. 8; and
 (iii) a combination of (i) and (ii).
29. Crystalline Form 3 of AMG-510 according to Clause 28, which is characterized by an X-ray powder diffraction pattern having peaks at 6.3, 8.4, 9.5, 16.0 and 17.6 degrees 2-theta±0.2 degrees 2-theta, and also having any one, two, three, four or five additional peaks selected from 10.4, 16.6, 18.8, 20.0 and 28.7 degrees 2-theta±0.2 degrees 2-theta.
30. Crystalline Form 3 of AMG-510 according to Clause 28 or Clause 29, which is characterized by an X-ray powder diffraction pattern having peaks at 6.3, 8.4, 9.5, 10.4, 16.0, 16.6, 17.6, 18.8, 20.0 and 28.7 degrees 2-theta±0.2 degrees 2-theta.
31. Crystalline Form 3 of AMG-510 according to any of Clauses 28, 29 or 30, which is an anhydrous form, optionally wherein the anhydrous form contains: 1 wt % or less, 0.75 wt % or less, 0.5 wt % or less, 0.25 wt % or less, or 0.1 wt % or less, of water or organic solvents.
32. A crystalline form of AMG-510, designated Form H3, which is characterized by data selected from one or more of the following:
 (i) an X-ray powder diffraction pattern having peaks at 5.4, 7.3, 18.1, 19.8 and 20.4 degrees 2-theta±0.2 degrees 2-theta;
 (ii) an X-ray powder diffraction pattern substantially as depicted in FIG. 9; and
 (iii) a combination of (i) and (ii).
33. Crystalline Form H3 of AMG-510 according to Clause 32, which is characterized by an X-ray powder diffraction pattern having peaks at 5.4, 7.3, 18.1, 19.8 and 20.4 degrees 2-theta±0.2 degrees 2-theta, and also having any one, two, three, four or five additional peaks selected from 14.5, 16.0, 16.6, 21.7 and 24.8 degrees 2-theta±0.2 degrees 2-theta.
34. Crystalline Form H3 of AMG-510 according to Clause 32 or Clause 33, which is characterized by an X-ray powder diffraction pattern having peaks at 5.4, 7.3, 14.5, 16.0, 16.6, 18.1, 19.8, 20.4, 21.7, and 24.8 degrees 2-theta±0.2 degrees 2-theta.

35. Crystalline Form H3 of AMG-510 according to any of Clauses 32, 33 or 34, which is a hydrate form.

36. AMG-510 succinate.

37. AMG-510 succinate according to Clause 36 wherein the ratio of AMG-510 and succinic acid is between about 1:1 to about 1:2, and optionally 1:1.

38. AMG-510 succinate according to Clause 36 or Clause 37 which is crystalline.

39. Crystalline AMG-510 succinate according to Clause 38, designated Form S1, which is characterized by data selected from one or more of the following:
   (i) an X-ray powder diffraction pattern having peaks at 11.0, 14.5, 22.0, 23.2 and 26.0 degrees 2-theta±0.2 degrees 2-theta;
   (ii) an X-ray powder diffraction pattern substantially as depicted in FIG. 10; and
   (iii) a combination of (i) and (ii).

40. Crystalline form of AMG-510 succinate according to Clause 38 or Clause 39, which is characterized by an X-ray powder diffraction pattern having peaks at 11.0, 14.5, 22.0, 23.2 and 26.0 degrees 2-theta±0.2 degrees 2-theta, and also having any one, two, three or four additional peaks selected from 9.5, 17.2, 18.9 and 27.3 degrees 2-theta±0.2 degrees 2-theta.

41. Crystalline form of AMG-510 succinate according to any of Clauses 38, 39 or 40, which is characterized by an X-ray powder diffraction pattern having peaks at 9.5, 11.0, 14.5, 17.2, 18.9, 22.0, 23.2, 26.0, 27.3 degrees 2-theta±0.2 degrees 2-theta.

42. Crystalline form of AMG-510 succinate according to any of Clauses 38, 39, 40, or 41, which is an anhydrous form, optionally wherein the anhydrous form contains: 1 wt % or less, 0.75 wt % or less, 0.5 wt % or less, 0.25 wt % or less, or 0.1 wt % or less, of water or organic solvents.

43. A crystalline form of AMG-510, designated Form C, which is characterized by data selected from one or more of the following:
   (i) an X-ray powder diffraction pattern having peaks at 7.1, 9.0, 10.5, 14.1 and 16.6 degrees 2-theta±0.2 degrees 2-theta;
   (ii) an X-ray powder diffraction pattern substantially as depicted in at least one of FIGS. 11-14; and
   (iii) a combination of (i) and (ii).

44. Crystalline Form C of AMG-510 according to Clause 43, which is characterized by an X-ray powder diffraction pattern having peaks at 7.1, 9.0, 10.5, 14.1 and 16.6 degrees 2-theta±0.2 degrees 2-theta, and also having any one, two, three or four additional peaks selected from 9.8, 13.7, 17.4 and 21.3 degrees 2-theta±0.2 degrees 2-theta.

45. Crystalline Form C of AMG-510 according to Clause 43 or Clause 44, which is characterized by an X-ray powder diffraction pattern having peaks at 7.1, 9.0, 9.8, 10.5, 13.7, 14.1, 16.6, 17.4, and 21.3 degrees 2-theta±0.2 degrees 2-theta.

46. Crystalline Form C of AMG-510 according to any of Clauses 43, 44 or 45, which is a solvate form, optionally wherein crystalline Form C is selected from: a 2-propanol solvate, designated Form C1; an acetone solvate, designated Form C2; a tetrahydrofuran solvate, designated Form C3; and a methyl ethyl ketone solvate designated Form C4.

47. A crystalline form of AMG-510, designated Form H4, which is characterized by data selected from one or more of the following:
   (i) an X-ray powder diffraction pattern having peaks at 5.8, 7.7, 11.5, 12.0 and 19.1 degrees 2-theta±0.2 degrees 2-theta;
   (ii) an X-ray powder diffraction pattern substantially as depicted in FIG. 15; and
   (iii) a combination of (i) and (ii).

48. Crystalline Form H4 of AMG-510 according to Clause 47, which is characterized by an X-ray powder diffraction pattern having peaks at 5.8, 7.7, 11.5, 12.0 and 19.1 degrees 2-theta±0.2 degrees 2-theta, and also having any one, two, three, four or five additional peaks selected from 14.3, 16.1, 18.3, 21.8 and 24.0 degrees 2-theta±0.2 degrees 2-theta.

49. Crystalline Form H4 of AMG-510 according to Clause 47 or Clause 48, which is characterized by an X-ray powder diffraction pattern having peaks at 5.8, 7.7, 11.5, 12.0, 14.3, 16.1, 18.3, 19.1, 21.8 and 24.0 degrees 2-theta±0.2 degrees 2-theta.

50. Crystalline Form H4 of AMG-510 according to any of Clauses 47, 48 or 49, which is a hydrate form, optionally a monohydrate.

51. A crystalline form of AMG-510, designated Form D, which is characterized by data selected from one or more of the following:
   (i) an X-ray powder diffraction pattern having peaks at 6.9, 8.2, 11.5, 17.3 and 18.3 degrees 2-theta±0.2 degrees 2-theta;
   (ii) an X-ray powder diffraction pattern substantially as depicted in FIG. 16; and
   (iii) a combination of (i) and (ii).

52. Crystalline Form D of AMG-510 according to Clause 51, which is characterized by an X-ray powder diffraction pattern having peaks at 6.9, 8.2, 11.5, 17.3 and 18.3 degrees 2-theta±0.2 degrees 2-theta, and also having any one, two, three or four additional peaks selected from 9.7, 12.4, 15.1, and 20.9 degrees 2-theta±0.2 degrees 2-theta.

53. Crystalline Form D of AMG-510 according to Clause 51 or Clause 52, which is characterized by an X-ray powder diffraction pattern having peaks at 6.9, 8.2, 9.7, 11.5, 12.4, 15.1, 17.3, 18.3, and 20.9 degrees 2-theta±0.2 degrees 2-theta.

54. Crystalline Form D of AMG-510 according to any of Clauses 51, 52 or 53, which is a solvated form or a hydrate, optionally wherein the crystalline Form D of AMG-510 is an ethanol solvate.

55. A crystalline form of AMG-510, designated Form 4, which is characterized by characterized by data selected from one or more of the following:
   (i) an X-ray powder diffraction pattern having peaks at 12.6, 13.8, 14.8, 17.6 and 22.6 degrees 2-theta±0.2 degrees 2-theta;
   (ii) an X-ray powder diffraction pattern substantially as depicted in FIG. 17 or FIG. 18;
   (iii) a solid state $^{13}C$ NMR spectrum having signals at about 14.46, 30.10, 48.26, 121.27 and 135.42±0.2 ppm;
   (iv) a solid state $^{13}C$ NMR spectrum having the following chemical shift absolute differences from a peak at 42.45 ppm±1 ppm of: 27.99, 12.35, 5.81, 78.82 and 92.97 ppm±0.1 ppm;
   (v) a solid state $^{3}C$ NMR spectrum substantially as depicted in FIG. 19; or (vi) a combination of any or one or more of (i), (ii), (iii), (iv), and (v).

56. Crystalline Form 4 of AMG-510 according to Clause 55, which is characterized by:

an X-ray powder diffraction pattern having peaks at 6.3 12.6, 13.8, 14.8, 17.6 and 22.6 degrees 2-theta±0.2 degrees 2-theta; or an X-ray powder diffraction pattern having peaks at 8.3, 12.6, 13.8, 14.8, 17.6 and 22.6 degrees 2-theta±0.2 degrees 2-theta; or an X-ray powder diffraction pattern having peaks at 9.4, 12.6, 13.8, 14.8, 17.6 and 22.6 degrees 2-theta±0.2 degrees 2-theta.

57. Crystalline Form 4 of AMG-510 according to Clause 55, which is characterized by:

an X-ray powder diffraction pattern having peaks at 6.3, 8.3, 12.6, 13.8, 14.8, 17.6 and 22.6 degrees 2-theta±0.2 degrees 2-theta;

an X-ray powder diffraction pattern having peaks at 6.3, 9.4, 12.6, 13.8, 14.8, 17.6 and 22.6 degrees 2-theta±0.2 degrees 2-theta; or an X-ray powder diffraction pattern having peaks at 8.3, 9.4, 12.6, 13.8, 14.8, 17.6 and 22.6 degrees 2-theta±0.2 degrees 2-theta.

58. Crystalline Form 4 of AMG-510 according to Clause 55, which is characterized by an X-ray powder diffraction pattern having peaks at 6.3, 8.3, 9.4, 12.6, 13.8, 14.8, 17.6 and 22.6 degrees 2-theta±0.2 degrees 2-theta.

59. Crystalline Form 4 of AMG-510 according to Clause 55, which is characterized by an X-ray powder diffraction pattern having peaks at 12.6, 13.8, 14.8, 17.6 and 22.6 degrees 2-theta±0.2 degrees 2-theta, and also having any one, two, three, four or five additional peaks selected from 6.3, 8.3, 9.4, 18.0 and 25.1 degrees 2-theta±0.2 degrees 2-theta.

60. Crystalline Form 4 of AMG-510 according to Clause 55, which is characterized by an X-ray powder diffraction pattern having peaks at 6.3, 8.3, 9.4, 12.6, 13.8, 14.8, 17.6, 18.0, 22.6, and 25.1 degrees 2-theta 0.2 degrees 2-theta.

61. Crystalline Form 4 of AMG-510 according to Clause 55 which is characterized by an X-ray powder diffraction pattern having peaks at 12.6, 13.8, 14.8, 17.6 and 22.6 degrees 2-theta±0.2 degrees 2-theta, and also having any one, two, three, four or five additional peaks selected from 6.3, 8.3, 9.4, 18.0 and 25.1 degrees 2-theta±0.2 degrees 2-theta as well as any one peak at: 7.4, 10.0, 11.3, 11.5, 17.1 degrees 2-theta±0.2 degrees 2-theta.

62. Crystalline Form 4 of AMG-510 according to Clause 55 or Clause 61, which is further characterized by an X-ray powder diffraction pattern having peaks at 6.3, 8.3, 9.4, 12.6, 13.8, 14.8, 17.6, 18.0, 22.6, and 25.1 degrees 2-theta 0.2 degrees 2-theta, and any one peak at: 7.4, 10.0, 11.3, 11.5, 17.1 degrees 2-theta±0.2 degrees 2-theta.

63. Crystalline Form 4 of AMG-510 according to Clause 55, which is characterized by an X-ray powder diffraction pattern having peaks at 12.6, 13.8, 14.8, 17.6 and 22.6 degrees 2-theta±0.2 degrees 2-theta, and also having any one, two, three, four or five additional peaks selected from 7.4, 10.0, 11.3, 11.5, 17.1 degrees 2-theta±0.2 degrees 2-theta.

64. Crystalline Form 4 of AMG-510 according to Clause 63, which is characterized by an X-ray powder diffraction pattern having peaks at 7.4, 10.0, 11.3, 11.5, 12.6, 13.8, 14.8, 17.1, 17.6 and 22.6 degrees 2-theta±0.2 degrees 2-theta.

65. Crystalline Form 4 of AMG-510 according to any of Clauses 55, 56, 57, 58, 59, 60, 61, 62, 63 or 64, which is further characterized by an XPRD pattern having an absence of a peak at any one of 8.8, 9.0, 10.4, 10.8, 18.7, and 19.8 degrees 2-theta±0.2 degrees 2-theta.

66. Crystalline Form 4 of AMG-510 according to any of Clauses 55, 56, 57, 58, 59, 60, 61, 62, 63, 64, or 65, which is further characterized by an XPRD pattern having an absence of a peak at any one of 8.8, 9.0, 10.4, 10.8, and 19.8 degrees 2-theta±0.2 degrees 2-theta.

67. Crystalline Form 4 of AMG-510 according to any of Clauses 55, 56, 57, 58, 59, 60, 61, 62, 63, 64, 65, or 66, which is further characterized by an XPRD pattern having an absence of a peak at any one or more of 8.8, 9.0, 10.4, 10.8, and 19.8 degrees 2-theta±0.2 degrees 2-theta.

68. Crystalline Form 4 of AMG-510 according to any of Clauses 55, 56, 57, 58, 59, 60, 61, 62, 63, 64, 65, 66, or 67, which is further characterized by an XRPD pattern having an absence of peaks at 8.8, 9.0, 10.4, 10.8, 18.7, and 19.8 degrees 2-theta±0.2 degrees 2-theta.

69. Crystalline Form 4 of AMG-510 according to any of Clauses 55, 56, 57, 58, 59, 60, 61, 62, 63, 64, 65, 66, 67, or 68, which is further characterized by a solid state $^{13}C$ NMR spectrum having signals at about 14.46, 30.10, 48.26, 121.27 and 135.42±0.2 ppm.

70. Crystalline Form 4 of AMG-510 according to any of Clauses 55, 56, 57, 58, 59, 60, 61, 62, 63, 64, 65, 66, 67, 68, or 69, which is further characterized by a solid state $^{13}C$ NMR spectrum having the following chemical shift absolute differences from a peak at 42.45 ppm±1 ppm of: 27.99, 12.35, 5.81, 78.82 and 92.97 ppm±0.1 ppm.

71. Crystalline Form 4 of AMG-510 according to any of Clauses 55, 56, 57, 58, 59, 60, 61, 62, 63, 64, 65, 66, 67, 68, 69, or 70, which is further characterized by a solid state $^{3}C$ NMR spectrum substantially as depicted in FIG. 19.

72. Crystalline Form 4 of AMG-510 according to any of Clauses 55, 56, 57, 58, 59, 60, 61, 62, 63, 64, 65, 66, 67, 68, 69, 70, or 71, which is an anhydrous form.

73. Crystalline Form 4 of AMG-510, according to Clause 72, wherein the anhydrous form contains: 2 wt % or less, 1.8 wt % or less, 1.6 wt % or less, 1.5 wt % or less, 1.2 wt % or less, 1 wt % or less, 0.75 wt % or less, 0.5 wt % or less, 0.25 wt % or less, or 0.1 wt % or less, of water or organic solvents.

74. A product according to any of Clauses 1 to 73, which is isolated.

75. A product according to any of Clauses 1 to 74, which is polymorphically pure.

76. A product according to any of Clauses 1 to 75, which contains: no more than about 20%, no more than about 10%, no more than about 5%, no more than about 2%, no more than about 1%, or about 0% of any other solid state forms of the product.

77 Use of a product according to any of Clauses 1 to 76, for preparing other crystalline forms of AMG-510, salts of AMG-510 or crystalline forms thereof, or solvates of AMG-510 or crystalline forms thereof.

78. Use of a product according to any of Clauses 1 to 76, for preparing pharmaceutical compositions of AMG-510 or salts of AMG-510.

79. A pharmaceutical composition comprising a product according to any of Clauses 1 to 76 and at least one pharmaceutically acceptable excipient.
80. Use of a product according to any of Clauses 1 to 76, for the preparation of a pharmaceutical composition and/or formulation, preferably wherein the pharmaceutical formulation is for oral administration, and more preferably wherein the pharmaceutical composition is a solid dosage form, particularly a tablet or a capsule.
81. A process for preparing the pharmaceutical composition according to Clause 79, comprising combining a product according to any of Clauses 1 to 76 with at least one pharmaceutically acceptable excipient.
82. A product according to any of Clauses 1 to 76 or a pharmaceutical composition according to Clause 79, for use as a medicament.
83. A product according to any of Clauses 1 to 76 or a pharmaceutical composition according to Clause 79, for use according to Clause 82, in the treatment of KRAS G12C-mutant tumours; particularly KRAS G12C-mutant solid tumours; particularly non-small-cell lung cancer, colorectal cancer, pancreatic cancer, appendiceal cancer, endometrial cancer, and melanoma; more particularly in the treatment of non-small-cell lung cancer or colorectal cancer; or in the treatment of advanced or metastatic non-small-cell lung cancer or colorectal cancer, and more particularly locally advanced or metastatic non-small-cell lung cancer or colorectal cancer, and especially in the treatment of advanced or metastatic non-small-cell lung cancer or colorectal cancer following at least one prior systemic therapy.
84. A method of treating KRAS G12C-mutant tumours; particularly KRAS G12C-mutant solid tumours; particularly non-small-cell lung cancer, colorectal cancer, pancreatic cancer, appendiceal cancer, endometrial cancer, and melanoma; more particularly in the treatment of non-small-cell lung cancer or colorectal cancer; or in the treatment of advanced or metastatic non-small-cell lung cancer or colorectal cancer, and more particularly locally advanced or metastatic non-small-cell lung cancer or colorectal cancer, and especially in the treatment of advanced or metastatic non-small-cell lung cancer or colorectal cancer following at least one prior systemic therapy, wherein the method comprises administering a therapeutically effective amount of a crystalline product according to any of Clauses 1 to 76 or a pharmaceutical composition according to Clause 79, to a subject in need of the treatment.

Having thus described the disclosure with reference to particular preferred embodiments and illustrative examples, those in the art can appreciate modifications to the disclosure as described and illustrated that do not depart from the spirit and scope of the disclosure as disclosed in the specification. The Examples are set forth to aid in understanding the disclosure but are not intended to, and should not be construed to limit its scope in any way.

Powder X-Ray Diffraction ("XRPD") Method

Sample after being powdered in a mortar and pestle is applied directly on a silicon plate holder. The X-ray powder diffraction pattern was measured with Philips X'Pert PRO X-ray powder diffractometer, equipped with Cu irradiation source=1.54184 Å (Angstrom), X'Celerator (2.022° 2θ) detector. Scanning parameters: angle range: 3-40 deg., step size 0.0167, time per step 37 s, continuous scan. Peak positions were determined without using silicon powder as an internal standard.

Solid-State NMR (13C NMR) Method

Solid-state NMR spectra were acquired on Bruker Avance NEO 400 MHz NMR spectrometer equipped with 4.0 mm dual resonance HX CPMAS iProbe. Larmor frequencies of proton, carbon and nitrogen nuclei were 400, 100 and 40 MHz, respectively. 1H and 13C NMR chemical shifts are reported relative to TMS (δ 0.0 ppm). Chemical shifts were referenced using adamantane as an external reference for tetramethylsilane (TMS), setting the CH2 signal to 38.48 ppm. 15N NMR chemical shifts are reported relative to liquid ammonia (δ N 0.0 ppm). Samples were pressed in a 4.0 mm diameter ZrO2 rotors and sealed with Kel-F caps. Spinning rates were 15 000 for 1H MAS and 10 000 Hz for 13C and 15N CP-MAS experiments.

EXAMPLES

Preparation of Starting Materials

AMG-510 can be prepared according to methods known from the literature, for example, U.S. Pat. No. 10,519,146.

Example 1: Preparation of AMG-510 Amorphous

AMG-510 (250 mg) was suspended in 55 ml of ethyl acetate at reflux temperature (77° C.). Small amount of leftover precipitate was filtrated off over black ribbon filter paper. Obtained clear solution was placed on rotary evaporator. Obtained yellow powder was analyzed by XRPD. AMG-510 amorphous was obtained.

Example 2. Preparation of AMG-510 Amorphous

AMG-510 (400 mg) was dissolved in 20 ml of acetic acid at 63° C. Solution was spontaneously cooled down to room temperature (25° C.). 50 ml of water was added dropwise to the solution at room temperature. Obtained clear solution was placed on rotary evaporator. Obtained yellow powder was analyzed by XRPD. AMG-510 amorphous was obtained.

Example 3. Preparation of AMG-510 Amorphous

AMG-510 (2.510 g) was placed in zirconium oxide milling jar with seven zirconium oxide balls. Jar was placed on planetary ball mill. The sample was milled for 2 hours with frequency of 700 rpm. Obtained yellow powder was analyzed by XRPD. AMG-510 amorphous was obtained.

Example 4. Preparation of AMG-510 Form 1

Amorphous AMG-510 (305 mg) prepared according to Example 1. was suspended in 10 ml of n-heptane at 95° C. for 3 hours. Heating was turned off and suspension spontaneously cooled down to room temperature (25° C.) and it was additionally stirred for 16 hours. Suspension was filtrated off over blue ribbon filter paper on Hirsch funnel with vacuum. Obtained powder was analyzed by XRPD. AMG-510 Form 1 was obtained.

Example 5. Preparation of AMG-510 Form A

Amorphous AMG-510 (350 mg) prepared according to Example 1, was suspended in 3.5 ml of acetonitrile at room temperature (25° C.) for 3 days. Suspension was filtrated off over blue ribbon filter paper on Hirsch funnel with vacuum. Obtained powder was analyzed by XRPD. AMG-510 Form A was obtained.

Example 6. Preparation of AMG-510 Form B

Amorphous AMG-510 (350 mg) prepared according to Example 1, was suspended in 3.5 ml of dichloromethane at room temperature (25° C.) for 3 days. Suspension was filtrated off over blue ribbon filter paper on Hirsch funnel with vacuum. Obtained powder was analyzed by XRPD. AMG-510 Form B was obtained.

Example 7. Preparation of AMG-510 Form 2

AMG-510 Form A, obtained according to Example 5, was dried for 4 hours on 50° C. with vacuum and then it was analyzed by XRPD. AMG-510 Form 2 was obtained.

Example 8. Preparation of AMG-510 Form 2

AMG-510 Form B, obtained according to Example 6, was dried for 4 hours on 50° C. with vacuum and then it was analyzed by XRPD. AMG-510 Form 2 was obtained.

Example 9. Preparation of AMG-510 Form 2

Amorphous AMG-510 (350 mg) prepared according to Example 1, was suspended in 3.5 ml of methanol at room temperature (25° C.) for 3 days. Suspension was filtrated off over blue ribbon filter paper on Hirsch funnel with vacuum. Obtained powder was analyzed by XRPD. AMG-510 Form 2 (methanol solvate) was obtained. Obtained powder was dried for 5 hours on 60° C. with vacuum and then it was analyzed by XRPD. Anhydrous AMG-510 Form 2 was obtained.

Example 10. Preparation of AMG-510 Form H1

Amorphous AMG-510 (300 mg) was dissolved in 35 ml of acetone/water (1:1) solvent mixture at 52° C. Leftover precipitate was filtrated off over black ribbon filter paper. Obtained clear solution was cooled to 0° C. and stirred for 1 hour. Obtained white powder was filtrated off over black ribbon filter paper with vacuum and analyzed by XRPD. AMG-510 form H1 was obtained.

Example 11. Preparation of AMG-510 Form H2

AMG-510, Form 1 (50 mg) was dissolved in 5 ml of acetone/water (1:1) solvent mixture at reflux temperature (around 56° C.). Leftover precipitate was filtrated off over black ribbon filter paper. Obtained clear solution was left to cool to room temperature. Obtained white powder was filtrated off over black ribbon filter paper with vacuum and analyzed by XRPD. AMG-510 form H2 was obtained.

Example 12. Preparation of AMG-510 Form 3

AMG-510 Form H1, obtained according to Example 10, was dried for 2 hours on 40° C. with vacuum and then it was analyzed by XRPD. AMG-510 Form 3 was obtained.

Example 13. Preparation of AMG-510 Form 3

AMG-510 Form H2, obtained according to Example 11, was dried for 5 hours on 65° C., and additional 2 hours on 80° C. with vacuum and then it was analyzed by XRPD. AMG-510 Form 3 was obtained.

Example 14. Preparation of AMG-510 Form H3

AMG-510 Form 2 (100 mg) was suspended in 1 ml of water at room temperature (24° C.) for 6 days. Obtained white powder was filtrated off over black ribbon filter paper with vacuum and analyzed by XRPD. AMG-510 Form H3 was obtained.

Example 15. Preparation of AMG-510: Succinic Acid Form S1

Amorphous AMG-510 (200 mg) was dissolved in 8 ml of acetone at reflux temperature. 22 mg (0.5 equivalents) of succinic acid were added to the solution at reflux temperature. Obtained clear solution was cooled to 30° C. 3 mL of MIBK was added dropwise to the solution at 30° C. Obtained solution was spontaneously left to cool to room temperature. Approximately half of reaction mixture volume was evaporated on rota-vapour and suspension was obtained. Additional 2 mL of MIBK was added to the obtained suspension and suspension was left to stir overnight at room temperature (24° C.). Obtained white powder was filtrated off over black ribbon filter paper with vacuum and washed with 6 portions of 0.5 mL of acetone, and analyzed by XRPD. AMG-510: succinic acid form S1 was obtained.

Example 16. Preparation of AMG-510 Form C

Amorphous AMG-510 (300 mg) was suspended in 3 ml of 2-propanol, acetone, tetrahydrofuran or methyl ethyl ketone at room temperature (24° C.) for 4 days. Obtained white powder was filtrated off over black ribbon filter paper with vacuum and analyzed by XRPD. AMG-510 form C was obtained.

Example 17. Preparation of AMG-510 Form H4

AMG-510 Form H3 (50 mg) was dried in an oven under vacuum at 40° C. for 3 hours. Obtained powder was analyzed by XRPD. AMG-510 form H4 was obtained.

Example 18. Preparation of AMG-510 Form D

AMG-510 Form 3 (20 mg) was placed in an eppendorf tube. The tube was placed in bottle with 2 mL of ethanol and closed. Sample was exposed to ethanol vapor for 7 days at room temperature (24° C.). Obtained powder was analyzed by XRPD. AMG-510 form D was obtained.

Example 19. Preparation of AMG-510 Form 4

AMG-510 Form H4 (50 mg) was dried in oven under vacuum at 90° C. for 3 hours, and additionally at 100° C. for 5 hours. Obtained powder was analyzed by XRPD. AMG-510 form 4 was obtained.

Example 20. Preparation of AMG-510 Form 4

1 g of Sotorasib (Form 2) was suspended in 25 mL of water on room temperature (25° C.) for 18 hours. Obtained white powder was filtrated of over blue ribbon filter paper and dried in oven, under vacuum on 80° C. for 17 hours. It was analysed by XRPD and confirmed to be AMG-510 form 4.

The invention claimed is:

1. A crystalline Form 4 of AMG-510 which is characterized by data selected from one or more of the following:
 (i) an X-ray powder diffraction pattern having peaks at 9.4, 12.6, 13.8, 14.8, 17.6 and 22.6 degrees 2-theta±0.2 degrees 2-theta and an absence of peaks at 10.4 and 10.8 degrees 2-theta±0.2 degrees 2-theta;
 (ii) an X-ray powder diffraction pattern as depicted in FIG. 17 or FIG. 18;
 (iii) a solid state $^{13}C$ NMR spectrum having signals at about 14.46, 30.10, 48.26, 121.27 and 135.42±0.2 ppm;
 (iv) a solid state $^{13}C$ NMR spectrum having the following chemical shift absolute differences from a peak at 42.45 ppm±1 ppm of: 27.99, 12.35, 5.81, 78.82 and 92.97 ppm±0.1 ppm;
 (v) a solid state $^{13}C$ NMR spectrum as depicted in FIG. 19; or
 (vi) a combination of any or one or more of (i), (ii), (iii), (iv), and (v).

2. The crystalline Form 4 of AMG-510 according to claim 1, which is characterized by an X-ray powder diffraction pattern having peaks at 12.6, 13.8, 14.8, 17.6 and 22.6 degrees 2-theta±0.2 degrees 2-theta and an absence of a peaks at 10.4 and 10.8 degrees 2-theta±0.2 degrees 2-theta, and also having any one, two, three, or four additional peaks selected from 6.3, 8.3, 18.0 and 25.1 degrees 2-theta±0.2 degrees 2-theta.

3. The crystalline Form 4 of AMG-510 according to claim 1, which is further characterized by an XPRD pattern having any one, two, three, four or five additional peaks selected from 7.4, 10.0, 11.3, 11.5, 17.1 degrees 2-theta±0.2 degrees 2-theta.

4. The crystalline Form 4 of AMG-510 according to claim 1, which is further characterized by an XPRD pattern having an absence of a peak at any one of 8.8, 9.0, 18.7, and 19.8 degrees 2-theta±0.2 degrees 2-theta.

5. The crystalline Form 4 of AMG-510 according to claim 1, which is an anhydrous form.

6. The crystalline Form 4 of AMG-510 according to claim 5, wherein the anhydrous form contains 1 wt % or less of water or organic solvents.

7. The crystalline Form 4 according to claim 1, which is isolated.

8. The crystalline Form 4 according to claim 1, which is polymorphically pure.

9. The crystalline Form 4 according to claim 1, which contains no more than about 20% of any other solid state forms of the product.

10. The crystalline Form 4 according to claim 1, which contains from about 1% to about 20% (w/w) of one or more other crystalline polymorph of the same AMG-510.

11. A pharmaceutical composition comprising the crystalline Form 4 according to claim 1 and at least one pharmaceutically acceptable excipient.

12. A process for preparing a pharmaceutical composition, comprising combining the crystalline Form 4 according to claim 1 and at least one pharmaceutically acceptable excipient.

13. A medicament comprising the crystalline Form 4 according to claim 1.

14. A method of treating KRAS G12C-mutant tumours, non-small-cell lung cancer, colorectal cancer, pancreatic cancer, appendiceal cancer, endometrial cancer, or melanoma, comprising administering a therapeutically effective amount of the crystalline Form 4 according to claim 1 to a subject in need of the treatment.

* * * * *